(12) United States Patent
Lampropoulos et al.

(10) Patent No.: US 10,398,881 B2
(45) Date of Patent: Sep. 3, 2019

(54) INFLATION DEVICES WITH REMOTE DISPLAYS, METHODS AND KITS RELATED THERETO

(71) Applicant: Merit Medical Systems, Inc., South Jordan, UT (US)

(72) Inventors: Fred Lampropoulos, Salt Lake City, UT (US); Jim Mottola, Salt Lake City, UT (US); Blaine Johnson, Riverton, UT (US); Steven Weir, Sandy, UT (US); Rajeev Bhalla, Rockville, MD (US); Jeffrey Cameron Loper, Alexandria, VA (US); Drew Carlton, Alexandria, VA (US); Zachary Glickstein, Alexandria, VA (US)

(73) Assignee: Merit Medical Systems, Inc., South Jordan, UT (US)

( * ) Notice: Subject to any disclaimer, the term of this patent is extended or adjusted under 35 U.S.C. 154(b) by 881 days.

(21) Appl. No.: 14/449,506

(22) Filed: Aug. 1, 2014

(65) Prior Publication Data

US 2015/0038901 A1    Feb. 5, 2015

Related U.S. Application Data

(60) Provisional application No. 61/861,997, filed on Aug. 3, 2013.

(51) Int. Cl.
*A61M 25/10* (2013.01)
*A61M 25/00* (2006.01)
(Continued)

(52) U.S. Cl.
CPC ....... *A61M 25/10182* (2013.11); *A61M 5/486* (2013.01); *A61M 13/00* (2013.01);
(Continued)

(58) Field of Classification Search
CPC ...... A61M 25/10182; A61M 25/10188; A61M 5/486; A61M 2205/3344; A61M 16/044;
(Continued)

(56) References Cited

U.S. PATENT DOCUMENTS

| | | |
|---|---|---|
| D309,663 S | 7/1990 | Robinson |
| D330,078 S | 10/1992 | Porter |

(Continued)

FOREIGN PATENT DOCUMENTS

| | | |
|---|---|---|
| WO | 2011097487 | 8/2011 |
| WO | 2011119896 | 9/2011 |
| WO | 2015020895 | 2/2012 |

OTHER PUBLICATIONS

Charles Arthur, BlackBerry PlayBook launch date, Price and Specs revealed, The Guardian, Mar. 22, 2011, available online at https://www.theguardian.com/technology/2011/mar/22/blackberry-playbook-launch-date-price-specs.*

(Continued)

*Primary Examiner* — Amber R Stiles
(74) *Attorney, Agent, or Firm* — Stoel Rives LLP

(57) ABSTRACT

Inflation devices configured to communicate with remote displays are disclosed herein. Kits including such inflation devices with portable display devices are also disclosed herein. Methods of remotely displaying pressure data from a medical device are also disclosed herein. Devices, kits, and methods of connecting medical devices to remote displays and transferring information to or from linked computers are also disclosed.

15 Claims, 11 Drawing Sheets

(51) Int. Cl.
*A61M 13/00* (2006.01)
*A61M 16/04* (2006.01)
*A61M 5/48* (2006.01)
*G06F 19/00* (2018.01)

(52) U.S. Cl.
CPC ..... *A61M 16/044* (2013.01); *A61M 25/10188* (2013.11); *A61M 2025/0002* (2013.01); *A61M 2205/3344* (2013.01); *A61M 2205/3569* (2013.01); *A61M 2205/3584* (2013.01); *A61M 2205/3592* (2013.01); *A61M 2205/6063* (2013.01); *G06F 19/3468* (2013.01)

(58) Field of Classification Search
CPC .......... A61M 2205/3569; A61M 13/00; A61M 2205/6063; A61M 2205/3592; A61M 2205/3584; A61M 2025/0002; G06F 19/3468
See application file for complete search history.

(56) References Cited

U.S. PATENT DOCUMENTS

| | | | |
|---|---|---|---|
| D330,763 S | 11/1992 | Penny | |
| D331,107 S | 11/1992 | Kanner | |
| 5,215,523 A | 6/1993 | Williams et al. | |
| 5,259,838 A | 11/1993 | Taylor et al. | |
| 5,318,533 A | 6/1994 | Adams et al. | |
| 5,383,855 A | 1/1995 | Nicholson et al. | |
| 5,387,194 A | 2/1995 | Williams et al. | |
| 5,449,345 A * | 9/1995 | Taylor | G01D 9/00 604/100.03 |
| 5,453,091 A | 9/1995 | Taylor et al. | |
| 5,562,621 A * | 10/1996 | Claude | A61M 25/1018 604/100.03 |
| 5,647,847 A | 7/1997 | Lafontaine et al. | |
| 5,695,466 A | 12/1997 | Lopez et al. | |
| 6,139,523 A | 10/2000 | Taylor et al. | |
| D439,584 S | 3/2001 | Wang | |
| D440,575 S | 4/2001 | Wang | |
| 6,377,848 B1 | 4/2002 | Garde et al. | |
| 6,389,143 B1 | 5/2002 | Leedom et al. | |
| 6,394,977 B1 * | 5/2002 | Taylor | A61M 25/10 604/100.01 |
| D523,871 S | 6/2006 | Hally | |
| D524,321 S | 7/2006 | Hally | |
| D525,984 S | 8/2006 | Hally | |
| D528,124 S | 9/2006 | Hally | |
| D528,559 S | 9/2006 | Hally | |
| D534,916 S | 1/2007 | Hone | |
| D537,449 S | 2/2007 | Hoefnagels | |
| D550,691 S | 9/2007 | Hally | |
| 7,351,223 B2 | 4/2008 | Call | |
| D601,156 S | 9/2009 | Motohashi | |
| D627,365 S | 11/2010 | Brinda | |
| 7,892,202 B2 | 2/2011 | Lampropoulos et al. | |
| D676,060 S | 2/2013 | Frost | |
| D687,058 S | 7/2013 | Corcoran | |
| D690,318 S | 9/2013 | Kluttz | |
| D690,322 S | 9/2013 | Matas | |
| D693,463 S | 11/2013 | Burger | |
| D696,677 S | 12/2013 | Corcoran | |
| D697,204 S | 1/2014 | Maier | |
| D697,519 S | 1/2014 | Thomsen | |
| D701,226 S | 3/2014 | Jung | |
| D701,869 S | 4/2014 | Matas | |
| D702,723 S | 4/2014 | Abratowski | |
| D709,913 S | 7/2014 | Hurd | |
| D714,931 S | 10/2014 | Sealfon | |
| D720,449 S | 12/2014 | Galbraith | |
| 8,915,891 B2 | 12/2014 | Bornhoft | |
| D722,082 S | 2/2015 | Roberts | |
| D727,354 S | 4/2015 | Park | |
| D727,495 S | 4/2015 | Bown | |
| 9,003,816 B2 | 4/2015 | Stefanski | |
| D732,566 S | 6/2015 | Mitchell | |
| 9,058,696 B2 | 6/2015 | Omiya | |
| D740,300 S | 10/2015 | Lee | |
| D741,356 S | 10/2015 | Park | |
| D742,898 S | 11/2015 | Matas | |
| D606,085 S | 12/2015 | Agnetta | |
| D745,661 S | 12/2015 | Collins | |
| D748,126 S | 1/2016 | Sarukkai | |
| D749,092 S | 2/2016 | Lee | |
| D749,206 S | 2/2016 | Johnson | |
| 9,555,693 B2 | 1/2017 | Hopf et al. | |
| 2001/0023490 A1 | 9/2001 | Gloeckler et al. | |
| 2004/0122369 A1 | 6/2004 | Schriver et al. | |
| 2004/0176984 A1 | 9/2004 | White et al. | |
| 2004/0260238 A1 | 12/2004 | Call | |
| 2005/0148869 A1 * | 7/2005 | Masuda | A61M 5/14546 600/432 |
| 2006/0282062 A1 * | 12/2006 | Ishikawa | A61K 9/0024 604/890.1 |
| 2007/0112299 A1 | 5/2007 | Smit et al. | |
| 2007/0136679 A1 | 6/2007 | Yang | |
| 2007/0156595 A1 | 7/2007 | Balassanian | |
| 2007/0266344 A1 | 11/2007 | Olcott | |
| 2008/0086087 A1 | 4/2008 | Spohn et al. | |
| 2008/0250340 A1 * | 10/2008 | Dlugos | A61B 5/02055 715/771 |
| 2009/0281489 A1 * | 11/2009 | Lampropoulos | A61M 25/10188 604/97.03 |
| 2010/0217188 A1 | 8/2010 | Lampropoulos et al. | |
| 2010/0274180 A1 | 10/2010 | Donovan et al. | |
| 2011/0144419 A1 * | 6/2011 | Timm | A61F 5/0056 600/37 |
| 2011/0238082 A1 | 9/2011 | Wenderow et al. | |
| 2012/0116366 A1 | 5/2012 | Houser et al. | |
| 2013/0132028 A1 | 5/2013 | Crankson | |
| 2013/0132887 A1 | 5/2013 | Amin | |
| 2013/0197679 A1 | 8/2013 | Balakrishnan | |
| 2013/0310753 A1 | 11/2013 | Cabiri | |
| 2013/0310756 A1 * | 11/2013 | Whalley | A61M 5/31 604/189 |
| 2013/0324989 A1 | 12/2013 | Leung | |
| 2013/0331634 A1 * | 12/2013 | Kaintz | A61M 39/223 600/4 |
| 2014/0045010 A1 | 2/2014 | Myers et al. | |
| 2014/0275935 A1 * | 9/2014 | Walsh | A61F 9/026 600/398 |
| 2015/0038901 A1 | 2/2015 | Lampropoulos et al. | |
| 2015/0193553 A1 | 7/2015 | Petersen | |

OTHER PUBLICATIONS

U.S. Appl. No. 29/504,937, filed Oct. 10, 2014, Weir et al.
U.S. Appl. No. 29/504,954, filed Oct. 10, 2014, Carlton et al.
U.S. Appl. No. 29/504,961, filed Oct. 10, 2014, Carlton et al.
U.S. Appl. No. 14/608,904, filed Jan. 29, 2015, Lampropoulos et al.
International Search Report and Written Opinion dated Nov. 11, 2014 for PCT/US2014/049364.
Notice of Allowance dated Jan. 21, 2016 for U.S. Appl. No. 29/504,961.
Office Action dated Feb. 23, 2016 for U.S. Appl. No. 29/504,937.
International Search Report and Written Opinion dated May 12, 2016 for PCT/US2016014822.
Notice of Allowance dated Mar. 18, 2016 for U.S. Appl. No. 29/504,954.
Notice of Allowance dated Apr. 13, 2016 for U.S. Appl. No. 29/504,954.
Notice of Allowance dated Jun. 27, 2016 for U.S. Appl. No. 29/504,937.
International Search Report and Written Opinion dated Jun. 14, 2016 for PCT/US2016/020574.
U.S. Appl. No. 15/059,545, filed Mar. 3, 2016.
European Search Report dated Mar. 15, 2017 for EP148341993.
Notice of Allowance dated May 7, 2018 for U.S. Appl. No. 15/059,545.

(56) References Cited

OTHER PUBLICATIONS

Office Action dated Sep. 25, 2017 for U.S. Appl. No. 14/608,904.
European Search Report dated Jul. 3, 2018 for EP16759456.3.
Notice of Allowance dated Jun. 6, 2018 for U.S. Appl. No. 14/608,904.
European Search Report dated Aug. 23, 2018 for EP16743928.0.
European Search Report dated Mar. 22, 2019 for EP14834199.3.

\* cited by examiner

INFLATION DEVICES WITH REMOTE DISPLAYS, METHODS AND KITS RELATED THERETO

RELATED APPLICATIONS

This application claims priority to U.S. Provisional Application No. 61/861,997 titled "Inflation Devices with Remote Displays, Methods and Kits Related Thereto," filed on Aug. 3, 2013, which is hereby incorporated by reference in its entirety.

TECHNICAL FIELD

The present disclosure relates generally to devices used to pressurize, depressurize, or otherwise displace fluid, particularly in medical devices. More specifically, the present disclosure relates to remote displays for inflation devices and methods and kits related thereto.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
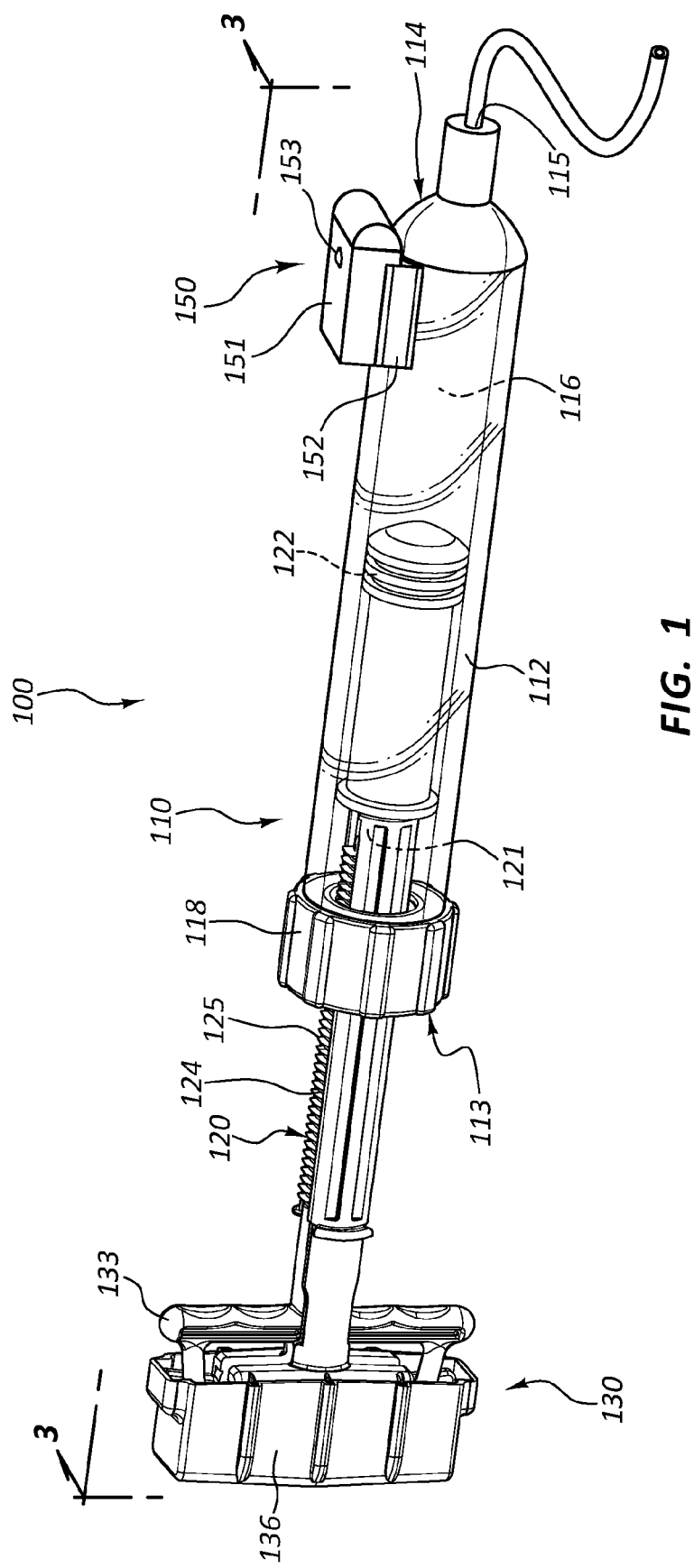
FIG. 1 is a perspective view of an inflation device with a pressure sensor and a wireless transmitter.

Inflation devices configured for use in connection with a medical device are disclosed herein. The inflation devices may comprise a body component and a pressurization component configured to increase or decrease pressure within the body component by displacing the pressurization component with respect to the body component. The inflation devices may further comprise an actuator operably connected to the pressurization component and configured to displace the body component. A pressure sensor may be in communication with the body component and configured to measure pressure within the body component. A transmitter may be in communication with the pressure sensor and configured to transmit a wireless signal representative of the pressure measured by the pressure sensor.

Inflation kits are also disclosed herein. The kits may comprise an inflation device disclosed herein and a portable display device configured to receive the wireless signal transmitted by the inflation device transmitter and also configured to display real-time pressure data within the body component.

Methods of remotely displaying pressure data from a medical device are also disclosed herein. The methods may comprise receiving a wireless signal from a medical device, transferring the wireless signal to a module configured to convert the wireless signal into pressure data, and presenting the pressure data on a display operably connected to the module.

It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," "in communication with," and "operably connected to" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component. With regard to wireless transfer of data between components which are wirelessly connected, coupled, or in communication with each other, any form of wireless interaction, including radio communication, optical communication, Bluetooth communication, Wi-Fi communication, infrared communication, sound wave transfer, and so forth are all within the scope of this disclosure.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the syringe portion of an inflation device, the proximal end of the syringe refers to the end nearest the handle and the distal end refers to the opposite end, the end nearest the inlet/outlet port of the syringe. Thus, if at one or more points in a procedure a physician changes the orientation of a syringe, as used herein, the term "proximal end" always refers to the handle end of the syringe (even if the distal end is temporarily closer to the physician).

"Fluid" is used in its broadest sense, to refer to any fluid, including both liquids and gases as well as solutions, compounds, suspensions, etc., that generally behave as fluids.

Figure 2:
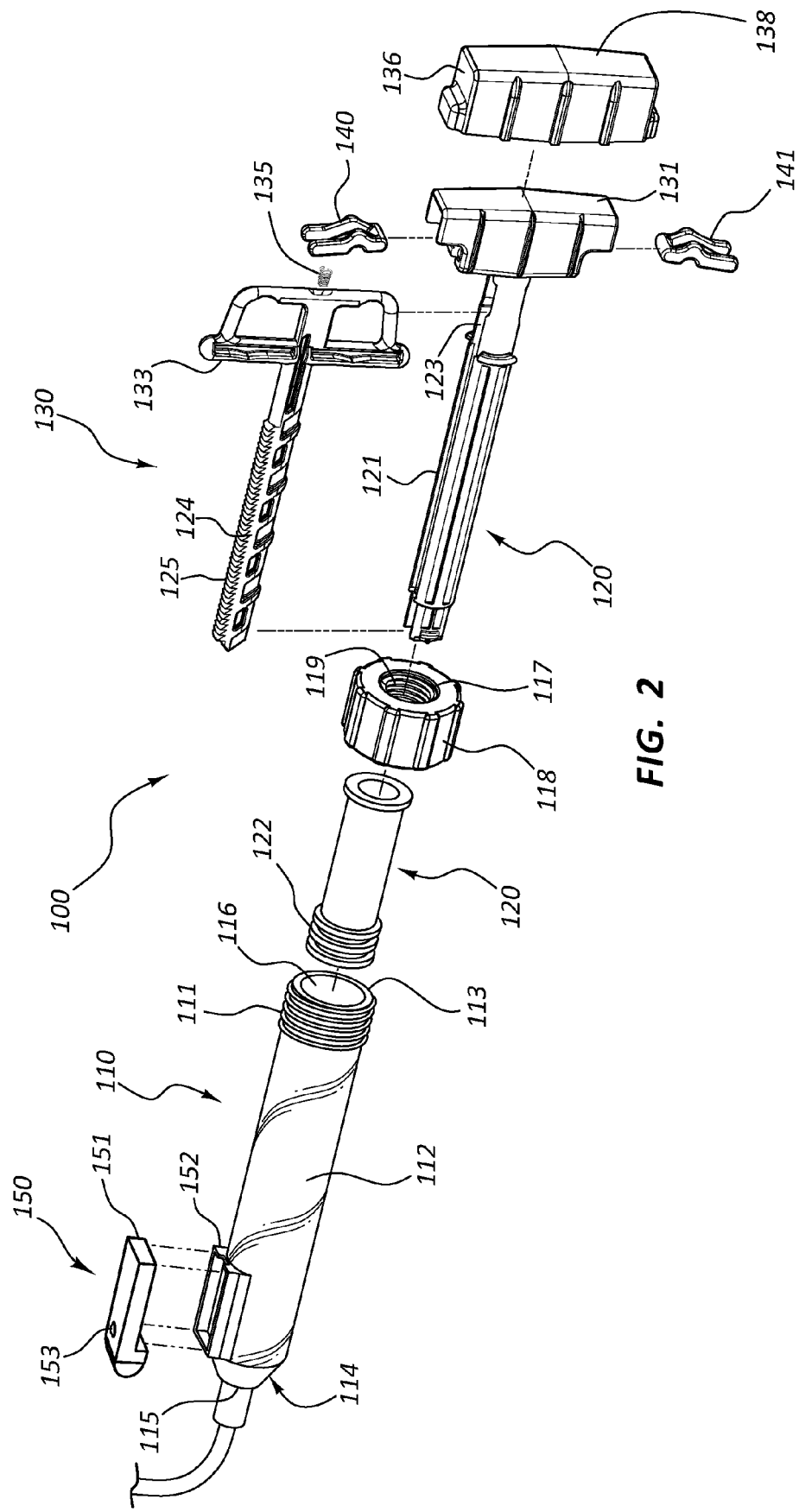
FIG. 2 is an exploded view of the inflation device of FIG. 1.
Figure 3:
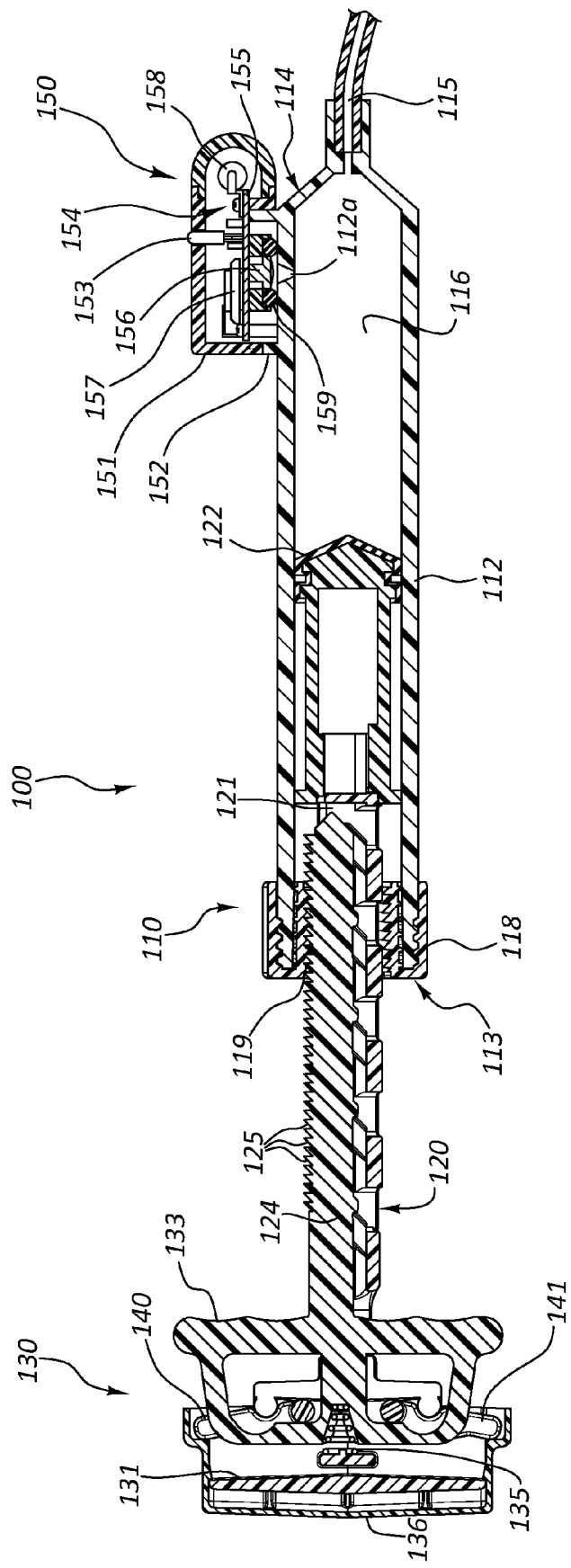
FIG. 3 is a cross sectional view of the inflation device of FIG. 1 taken through plane 3-3.

FIGS. 1-3 illustrate different views of an inflation device with a pressure sensor and a wireless transmitter. In certain views the device may be coupled to, or shown with, additional components not included in every view. In some views only selected components are illustrated, to provide detail regarding the relationship of the components. Some components may be shown in multiple views but not discussed in connection with every view. Disclosure provided in connection with any figure is relevant and applicable to disclosure provided in connection with any other figure. The devices, kits, and methods disclosed herein may be applicable to a variety of medical procedures, including inflation sequences, injection sequences, and so forth. Any concepts disclosed herein in connection with any particular procedure may be analogously applied to other medical procedures as well.

FIG. 1 is a perspective view of an inflation device 100. In the illustrated embodiment, the inflation device 100 is partially comprised of a syringe 110. The inflation device 100 includes four broad groups of components; each group may have numerous subcomponents and parts. The four broad component groups are: a body component such as syringe body 112, a pressurization component such as plunger 120, a handle 130, and a sensor component 150.

Referring to FIGS. 1-3, the sensor component 150 comprises a pressure sensor 156 and a transmitter 158. The transmitter 158 may be configured to transmit radio waves. For example, the transmitter 158 may be configured as a Bluetooth transmitter and/or as a Wi-Fi transmitter. One benefit of Bluetooth transmission is that the power consumption of the transmitter 158 is less than that of a Wi-Fi transmitter. The transmitter 158 may also be configured to transmit other forms of electromagnetic radiation instead of radio waves, such as, for example, infrared light. Still further, the transmitter 158 may be configured to transmit other waves or signals, for example, sound waves.

The transmitter 158 allows for wireless remote display of pressure signals generated by the pressure sensor 156. The ability to have a remote display may provide significant benefits to a doctor utilizing an inflation device. Space in the immediate vicinity of a patient's body during a medical procedure is at a premium, particularly the space near the insertion site of a catheter during an interventional procedure. When an inflation device is close to the insertion site, a display mounted on the inflation device may obscure a user's view of the insertion site and may block access to the insertion site by surgical staff. Additionally, a display mounted on an inflation device may only be visible to the individual using the inflation device.

One benefit of the transmitter 158 is that a signal representative of pressure data may be sent to a remote display device located in the operating room. The remote display device may then be placed away from the insertion site, thereby allowing a user of the inflation device a clear view of any stress being placed on the insertion site by a catheter or pressurization line. The remote display device may be located so as to not block access to the insertion site by surgical staff. Also, the remote display device may be located so as to be clearly visible to other surgical staff. This may allow multiple individuals to be aware of the pressure conditions of a medical device within the patient. This knowledge may in turn assist surgical staff to work as a team instead of waiting for instructions from the user of the inflation device.

The remote display may comprise a portable display. Any exemplary references herein to a portable display may be applied to any remote display, for example, desktop computers, fixed display screens, tablet computers, portable display screens, and so forth.

The syringe body 112 may be formed of a generally cylindrical hollow tube configured to receive the plunger 120. The syringe body 112 may include an inlet/outlet port 115 located adjacent the distal end 114 of the syringe body 112. In some embodiments, a coupling member 118 is coupled to the syringe body 112 adjacent the proximal end 113 of the syringe body 112. The coupling member 118 may include a center hole configured to allow the plunger 120 to pass through the coupling member 118 into the syringe body 112. Further, the coupling member 118 may include coupling member threads 119 (FIG. 2) configured to selectively couple the coupling member 118 to the plunger 120.

The plunger 120 may be configured to be longitudinally displaceable within the syringe body 112. The plunger 120 may be comprised of a plunger shaft 121 coupled to a plunger seal 122 at the distal end of the plunger shaft 121. The plunger shaft 121 may also be coupled to the handle 130 at the proximal end of the plunger shaft 121, with the plunger shaft 121 spanning the distance between the plunger seal 122 and the handle 130.

The handle 130 broadly refers to the group of components coupled to the proximal end of the plunger 120, some of which may be configured to be graspable by a user. In certain embodiments, the handle 130 is configured such that the user can manipulate the position of the plunger 120 by manipulating the handle 130. Further, in some embodiments, the handle 130 is an actuator mechanism configured to manipulate components of the inflation device 100.

Every component disclosed in connection with any of the exemplary handle configurations herein may be optional. That is, though the handle 130 broadly refers to the components coupled to the proximal end of the plunger shaft 121 that may be configured to be graspable by a user, use of the term "handle" is not meant to indicate that every disclosed handle component is always present. Rather, the term is used broadly, referring to the collection of components, but not specifically referring to or requiring the inclusion of any particular component. Likewise, other broad groupings of components disclosed herein, such as the syringe 110 or syringe body 112 and the plunger 120, may also refer to collections of individual subcomponents. Use of these terms should also be considered non-limiting, as each subcomponent may or may not be present in every embodiment.

As shown in FIG. 1, a fluid reservoir 116 may be defined by the space enclosed by the inside walls of the syringe body 112 between the plunger seal 122 and the distal end 114 of the syringe body 112. Accordingly, movement of the plunger seal 122 with respect to the syringe body 112 will alter the size and volume of the fluid reservoir 116.

As shown in FIGS. 1 and 2, in some embodiments, the syringe 110 includes a coupling member 118, fixedly coupled to the proximal end 113 of the syringe body 112. The coupling member 118 may utilize threads 117 or other coupling mechanisms to fixedly couple the coupling member 118 to corresponding threads 111 on the syringe body 112. The coupling member 118 may additionally include coupling member threads 119 configured to couple the coupling member 118 to a portion of the plunger 120. The plunger 120 may also include external plunger threads 125 configured to couple the plunger 120 to the coupling member 118. The plunger 120 may thus be translated longitudinally with respect to the syringe body 112 by rotating the plunger 120 such that the interaction of the coupling member threads 119 and the plunger threads 125 results in the longitudinal translation of the plunger 120. Thus, when the plunger threads 125 and the coupling member threads 119 are engaged, movement of the plunger 120 is constrained with respect to the syringe body 112, though the plunger 120 is not necessarily fixed with respect to the syringe body 112. For example, the plunger 120 may be rotatable, but not directly translatable, when the threads 125, 119 are engaged.

The plunger threads 125 may be configured such that they may be retracted within the plunger shaft 121. As shown in FIG. 3, in some embodiments, the plunger threads 125 do not extend 360 degrees around the axis of the plunger shaft 121. Furthermore, as shown in FIGS. 2 and 3, the plunger threads 125 may be formed on a thread rail 124, which may be disposed within a groove 123 in the plunger shaft 121.

Translation of the thread rail 124 in the proximal direction simultaneously causes the thread rail 124 to retract toward the center axis of the plunger shaft 121. Similarly, translation of the thread rail 124 in the distal direction causes the thread rail 124 to move away from the center axis of the plunger shaft 121 and toward threads 119 of the coupling member 118. In the illustrated embodiment, a distally oriented biasing force acting on the thread rail 124 biases the plunger threads 125 to the engaged position. Operation of the coupling member 118 and the thread rail 124 is further discussed in U.S. Patent Publication No. 2013-0123693, the contents of which are incorporated herein by reference in their entirety.

It will be appreciated by one of ordinary skill in the art having the benefit of this disclosure that it is within the scope of this disclosure to modify the angles and interfaces such that a distally oriented biasing force on the thread rail 124 would bias the plunger threads 125 in the retracted position. Analogous mechanisms are disclosed in U.S. Pat. Nos. 5,047,015, 5,057,078, 5,163,904, and 5,209,732, which are each incorporated by reference in their entireties.

The retractable threads may allow a user to displace the plunger shaft 121 relative to the syringe body 112 either through rotation of the plunger shaft 121 (and the subsequent interaction of threads), or by retracting the plunger threads 125 and displacing the plunger shaft 121 by applying opposing forces on the plunger shaft 121 and the syringe body 112. (The forces, of course, may move the plunger shaft 121 distally or proximally with respect to the syringe body 112.) Both methods of displacement may be utilized during the course of a single therapy.

In some instances, a practitioner may desire to quickly displace the plunger shaft 121, for instance, while priming the inflation device 100 or while priming or deflating an attached medical device such as a balloon. Quick displacement of the plunger shaft 121 may be accomplished by retracting the plunger threads 125 and sliding the plunger shaft 121 relative to the syringe body 112. For example, a practitioner may quickly fill the reservoir 116 with fluid by disengaging the plunger threads 125 and pulling the plunger shaft 121 in a proximal direction with respect to the syringe body 112. Further, a practitioner may quickly force fluid into lines leading to a medical device or quickly expel unwanted air bubbles from the reservoir 116 by retracting the plunger threads 125 and repositioning the plunger shaft 121.

In other instances, the practitioner may desire more precise control over the position of the plunger shaft 121 (for example when displacing the plunger shaft 121 in order to adjust the fluid pressure within the reservoir 116) or it may simply be difficult or impossible without a mechanical advantage to displace the plunger shaft 121 due to high fluid pressure within the reservoir 116. In these instances, the practitioner may opt to displace the plunger shaft 121 by rotation of the plunger shaft 121.

Similar principles of operation of the inflation device 100 may be achieved with different configurations of the inflation device 100. For example, the coupling member 118 may be integrally formed with the syringe body 112. In that embodiment threads 111 and threads 117 may not be present. In another example, the coupling member 118 may be rotatably coupled to the syringe body 112, such as via a rotatable hub. In such embodiments, rotation of the coupling member 118 inserts or retracts the plunger 120 within the syringe body 112 when the plunger 120 is engaged with the coupling member 118. For example, the coupling member 118 may be rotated counter-clockwise while the plunger shaft 121 is rotated clockwise to advance the plunger 120. The coupling member 118 may comprise additional features, such as levers, to facilitate mechanical advantage in the rotation of the coupling member 118.

In the illustrated embodiment, the inflation device 100 is configured to provide a mechanical advantage when engaging or disengaging the coupling member 118. Referring back to FIG. 3, the handle 130 of the inflation device 100 may include components that enable a practitioner to retract the thread rail 124 of the plunger 120. In some embodiments, the plunger shaft 121 is fixed to a first member such as inner member 131 of the handle 130. The thread rail 124 may be fixed to a trigger 133 component of the handle. Further, a biasing component 135 may be configured to bias the trigger 133 in a distal direction. Because the trigger 133 is fixed to the thread rail 124, a distally oriented force on the trigger 133 will result in a distally oriented force on the thread rail 124 as well. The force provided by the biasing component 135 (hereafter referred to as the biasing force) may thus bias the thread rail 124 in the engaged position as described above. Conversely, overcoming the biasing force and translating the trigger 133 in a proximal direction with respect to the plunger shaft 121 and inner member 131 may retract the plunger threads 125.

In some embodiments the handle 130 further includes a second member such as outer sleeve 136 and one or more levers 140, 141. The levers 140, 141 may be disposed such that they provide mechanical advantage, enabling the user to more easily overcome the biasing force and draw the trigger 133 toward the inner member 131. Any configuration for providing mechanical advantage in operation of an inflation device, such as the configurations disclosed in U.S. Patent Publication No. 2013-0123693, the contents of which are incorporated herein by reference in their entirety, may be used with the inflation devices disclosed herein, with the aid of the present disclosure.

A handle configured to provide a mechanical advantage when retracting a thread rail may be desirable for certain therapies that require large syringes or high pressure. Such therapies may also require a larger biasing force due to the size of the device or the pressure within the device. A handle providing a mechanical advantage may make devices configured for such therapies easier to use.

In some embodiments, the handle 130 is not configured to provide a mechanical advantage when disengaging the coupling member 118. For example, the levers 140 and 141 may not be present. In such embodiments, a user may need to directly overcome the biasing force of the biasing component 135 to disengage the plunger threads 125 of the thread rail 124 from the coupling member threads 119.

Many design modifications relating to the outer sleeve 136 are within the scope of the current disclosure. For example, in the illustrated embodiments, the outer sleeve 136 has a cap-like shape, fitting over the inner member 131. In other embodiments, the outer sleeve 136 is designed as a button that slides into the inner member 131 when it is compressed. Likewise, any other longitudinally actuatable component may be utilized in place of the outer sleeve 136.

The handle mechanism described above, and shown in each of FIGS. 2 and 3, may also be utilized to change the location and direction of an input force required to retract the plunger threads 125. Essentially, the mechanism allows a user to draw the trigger 133 toward the inner member 131 (and thus retract the threads) solely by applying a distally oriented force to the top surface 138 of the outer sleeve 136. As outlined above, the levers 140, 141 transfer this force to the trigger 133, which retracts the plunger threads 125.

In some instances a user, such as a medical practitioner, may desire to displace the plunger 120 in a distal direction with only one hand. This may be accomplished by grasping the syringe body 112 and using a surface, for example a table top, to apply a distally oriented force on the top surface 138 of the outer sleeve 136. In this manner, a mechanism such as that described above may enable a practitioner to displace the plunger in a one-handed fashion.

The sensor component 150 may comprise a housing 151 coupled to a mounting bracket 152 of the syringe body 112. The housing 151 may be configured to receive a sensor assembly 154 (FIG. 3). The sensor assembly 154 may comprise a pressure sensor 156 and a transmitter 158. The pressure sensor 156 may be configured to measure the pressure within the syringe body 112. The pressure sensor 156 may comprise any number of known pressure sensors. For example, the pressure sensor 156 may be a transducer. In some embodiments, the pressure sensor 156 measures gauge pressure, such that when pressure within the syringe body 112 drops below atmospheric pressure, then the gauge reads a negative pressure. Additionally, the pressure sensor 156 may be sealed such that the reference pressure does not change with changes in environmental atmospheric pressure. The pressure sensor 156 may be a force collector such as a piezoresistive strain gauge, a capacitive diaphragm, an electromagnetic diaphragm, or a potentiometric gauge.

The sensor assembly 154 may comprise a circuit board 155 having a top surface and a bottom surface. The sensor assembly 154 may further comprise one or more connection points configured to connect components of the sensor assembly 154 with other components of the inflation device 100, such as the battery 157.

The housing 151 may comprise an interior portion configured to receive the circuit board 155 and other components of the sensor assembly 154. In some embodiments, the circuit board 155 is configured to be just smaller than the interior portion, allowing the circuit board 155 to fit within the interior portion.

The circuit board 155 and other components of the sensor assembly 154 may be configured to be coupled to the housing 151. In some embodiments, the sensor assembly 154 is coupled to the housing 151 through a snap fit connection. As used herein, snap fit-type connections refer very broadly to a wide variety of fits or connections, such as connections that rely on friction between component parts (as opposed to adhesive or mechanical fasteners) to couple the component parts. In some embodiments, snap fit connections comprise a groove or slot in a first component, configured to receive a second component. One or more protrusions, tabs, ridges, ribs, barbs, or other locking feature may be disposed such that the feature is deformed when the second component is pushed into the receiving portion of the second component. Once the second component is in place, the locking feature may return to its initial position and lock the second component in place.

A wide variety of features (e.g., protrusions, tabs, ridges, barbs, slots, channels, holes, and so on) may be configured for use in connection with a snap fit. In embodiments wherein the sensor assembly 154 is configured to snap fit into the housing 151, mating features are found on both components, or features are only identifiable on one of the two components. Still further, in some embodiments protruding-type locking elements (e.g., barbs, ridges, and so on) are on either or both components and receiving-type locking elements (e.g., grooves, slots, and so on) are on either or both components.

FIG. 3 illustrates one embodiment of a circuit board 155 being disposed within the interior portion of the housing 151. The pressure sensor 156 may be coupled directly to the circuit board 155. An o-ring 159 is also shown in connection with this assembly. Each component of this assembly may be configured to be coupled together through use of one or more snap fit connections. As shown in FIG. 3, the circuit board 155 may be configured to exert pressure on the o-ring 159 when the components are assembled. In some embodiments, this pressure results from positional constraints on the circuit board 155 by the snap fit connection. FIG. 3 also illustrates how an aperture 112a may provide fluid communication with the pressure sensor 156 when the device is assembled. In such embodiments, the transmitter 158 may be located on the top surface of the circuit board 155.

As shown in FIG. 3, the pressure sensor 156 may be coupled to the bottom surface of the circuit board 155. The pressure sensor 156 may be configured to be in direct fluid communication with the interior portion of the syringe body 112. Thus, in some embodiments, no secondary fluid—such as a gel—is disposed between the pressure sensor 156 and the interior portion of the syringe body 112. A system configured for use without a gel or secondary fluid may remove the risk that inconsistencies (such as bubbles or leaks) in the secondary fluid will undesirably alter sensor measurements.

A seal, such as the o-ring 159, may be configured to isolate the pressure sensor 156 from the outside environment. In other words, the seal may be positioned such that the pressure sensor 156 is in fluid communication with the interior portion of the syringe body 112 but not with other areas of pressure. In the illustrated embodiment, the o-ring 159 is configured to be disposed around the aperture 112a such that the o-ring 159 seals the fluid communication between the pressure sensor 156 and the aperture 112a when the inflation device 100 is assembled. In some embodiments the circuit board 155 and housing 151 are configured to exert compressive forces on the o-ring 159 when the circuit board 155 and housing 151 are coupled. In some instances the receiving portion of a snap fit design is positioned such that the circuit board 155 and/or housing 151 partially compress the o-ring 159 in order to be snapped into place.

Alternatively, the pressure sensor 156 may be coupled to the top surface of the circuit board 155 and a circuit board aperture provides communication between the bottom surface of the circuit board 155 and the pressure sensor 156. In such embodiments, the transmitter 158 may be located on the top surface of the circuit board 155 as well.

The sensor assembly 154 may further comprise a pull tab (not shown) configured to electrically isolate the battery 157 from the circuit board 155 when the pull tab is in place. The pull tab may be configured to be removable. The sensor assembly 154 may be configured to continuously transmit pressure data when the pull tab is removed. It should be understood that in embodiments where pressure sensor 156 is a digital sensor, then "continuously transmit" means to repeatedly transmit at a consistent interval. For example, the clock speed of a processor controlling the pressure sensor 156 may determine the frequency with which pressure data is collected by the pressure sensor 156.

As an alternative to a pull tab, the sensor assembly 154 may comprise an on/off switch configured to control conduction of electrical energy from the battery 157 to the circuit board 155. When the switch is in the "on" position, the sensor assembly 154 may be configured to continuously transmit pressure data. As a further alternative, the sensor assembly 154 may alternatively or additionally comprise a momentary switch. The momentary switch may be configured to transition the device from a power save mode to a full power mode. The momentary switch may comprise a momentary button or trigger.

Figure 4:
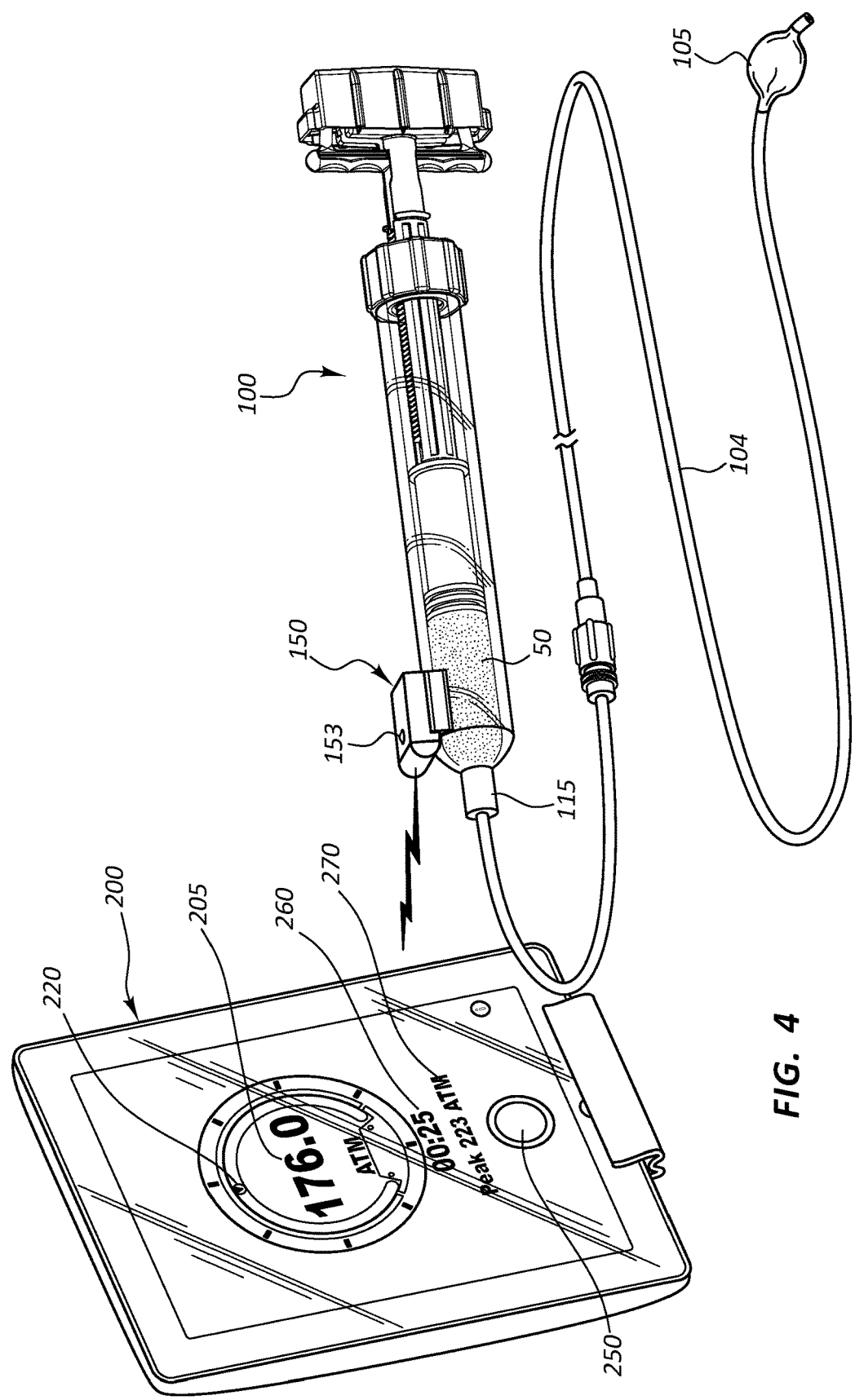
FIG. 4 is a perspective view of the inflation device of FIG. 1 with fluid disposed within the inflation device and a balloon coupled to the inflation device and a portable display device displaying the pressure within the inflation device.

FIG. 4 illustrates an embodiment of an inflation kit in use (without the user present). In the illustrated inflation kit, the inflation device 100 of FIG. 1 is coupled via a line 104 to a balloon 105. The syringe body 112 is filled with a fluid 50 for pressurizing the balloon 105. In the illustrated embodiment, the sensor component 150 is communicating with the portable display device 200.

Figure 5C:
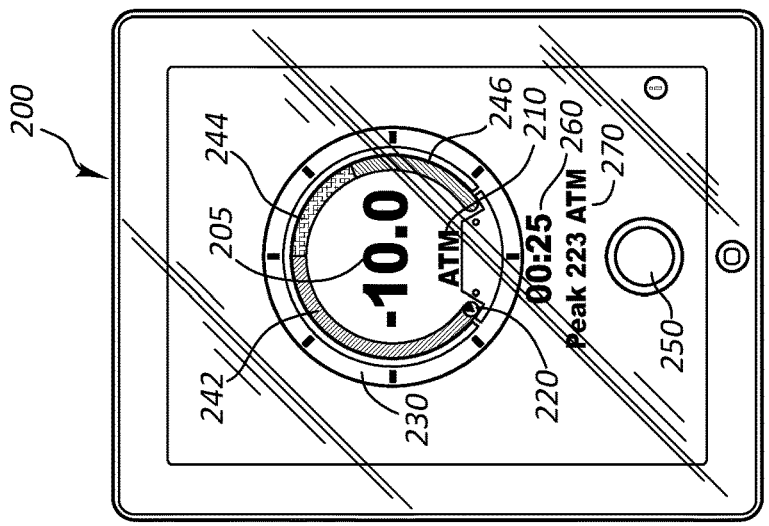
FIG. 5C is a front view of the portable display device of FIG. 4 displaying a negative pressure within the inflation device of FIG. 1, the time lapsed since the start of a medical procedure, and peak pressure during the immediately prior inflation.
Figure 5B:
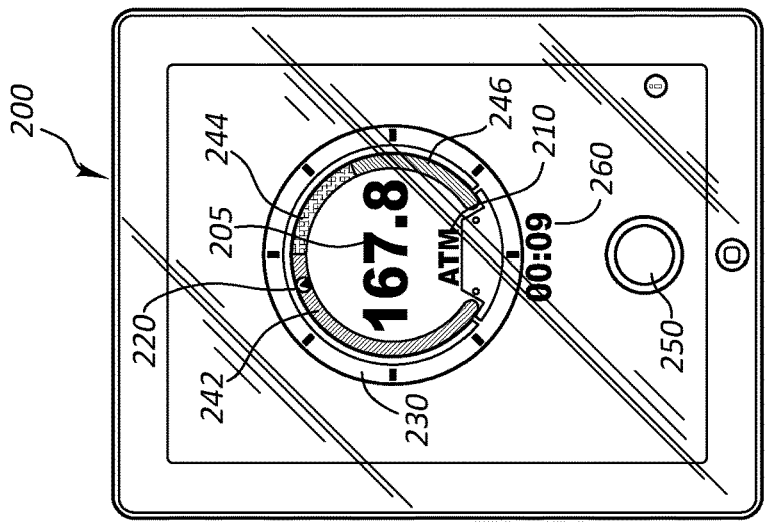
FIG. 5B is a front view of the portable display device of FIG. 4 displaying the current pressure within the inflation device of FIG. 1 and the time lapsed since the start of a medical procedure.
Figure 5A:
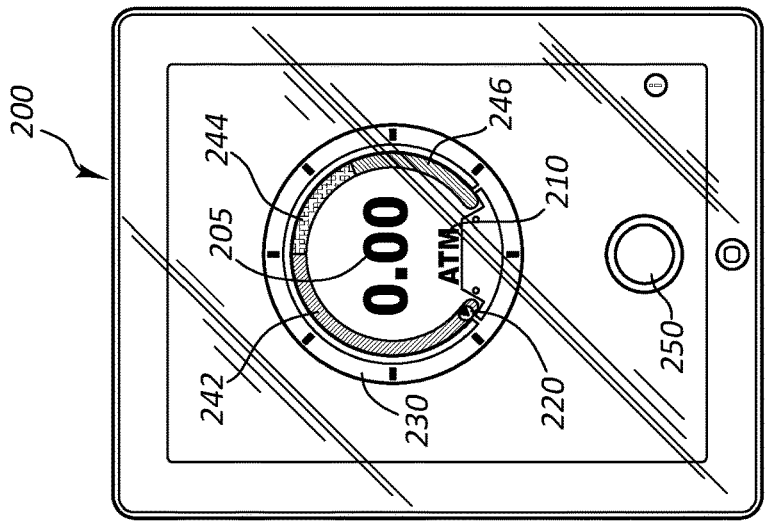
FIG. 5A is a front view of the portable display device of FIG. 4 displaying pressure within the inflation device of FIG. 1 before the start of a medical procedure.

The portable display device 200 may be configured to display a numeric pressure data 205, such as the 176.0 psi illustrated in FIG. 4, the 0.00 psi illustrated in FIG. 5A, the 167.8 psi illustrated in FIG. 5B, or the −10.0 psi illustrated in FIG. 5C. The numeric pressure data 205 may comprise a current inflation pressure of the fluid 50. In some embodiments the portable display device 200 may be configured to display pressure readings in general terms, or within certain increments. For example, the gauge may display pressure in increments of 5 ATM (e.g., 0-5, 5-10, and 10-15 ATM).

The portable display device 200 may also be configured to display a non-numeric indication of pressure data, such as the arrow 220. The non-numeric indication of pressure data may indicate whether the current pressure is likely safe for the medical device attached to the inflation device, which in the illustrated embodiment is the balloon 105 and inflation device 100, respectively. For example, in FIG. 5A, if the arrow 220 is in the region 242, then the pressure in the balloon 105 is unlikely to burst the balloon 105. The non-numeric indication of pressure data may indicate whether the current pressure is potentially unsafe for the medical device attached to the inflation device. For example, in FIG. 5A, if the arrow 220 is in the region 244, then the pressure in the balloon 105 may be sufficient to burst the balloon 105. The non-numeric indication of pressure data may also indicate whether the current pressure is likely unsafe for the medical device attached to the inflation device. For example, in FIG. 5A, if the arrow 220 is in the region 246, then the pressure in the balloon 105 is likely sufficient to burst the balloon 105. The regions 242, 244, and 246 may be color-coded to intuitively inform a user of the meaning of the different pressure regions. For example, the regions 242, 244, and 246 may be colored similar to the RPM (rotations per minute) gauge of an automobile. For example, the region 242 may be colored green, the region 244 may be colored yellow, and the region 246 may be colored red.

The portable display device 200 may also be configured to display additional non-numeric indications of pressure data, such as the markers 230. In the illustrated embodiment, markers 230 circumscribe the regions 242, 244, and 246. Each of the markers 230 represents approximately 45 psi of pressure. As the arrow 220 rotates along the regions 242, 244, and 246, the distance between the arrow 220 and the nearest marker 230 provides a user with a quick non-numerical sense of what the current pressure is.

The portable display device 200 may also be configured to display units 210 (FIGS. 5A-5C) listing the pressure units for the numeric pressure data 205. A user may be able to toggle to other pressure units, such as by touching the display units 210 when the portable display device 200 comprises a touchscreen.

The portable display device 200 may also be configured to display a clock 260 (FIG. 4) listing the elapsed time since the beginning of a medical procedure or an inflation sequence which comprises a portion of a medical procedure. The clock 260 may be configured to start when an inflation device begins transmitting a wireless signal or when the connect/disconnect button 250 is touched, as discussed in more detail below.

The portable display device 200 may also be configured to display a peak pressure 270 (FIG. 4). The peak pressure 270 may be the peak pressure from the most recent inflation of a medical device attached to an inflation device. For example, when a user is alternately inflating and deflating a medical device, and with each inflation increasing the pressure relative to the prior inflation, then having a ready display of the prior peak pressure may be useful.

The portable display device 200 may comprise a handheld computer, such as a tablet computer with a touchscreen graphic user interface. Examples of such a tablet computer include, but are not limited to, an iPad or an Android tablet. In the touchscreen embodiments, the portable display device 200 may also be configured to display a connect/disconnect button 250, such as illustrated in FIGS. 4-5C. An inflation device, such as the inflation device 100, may be configured to continuously transmit pressure data. In some instances, the portable display device 200 may be configured to only process the transmitted data after the connect/disconnect button 250 has been touched by a user. The portable display device 200 may be configured such that a user can initiate a connection (for example pair the portable display device 200 and an inflation device via Bluetooth) through interaction with one or both components. For example, when the portable display device 200 is not connected to an inflation device, then the connect/disconnect button 250 may display "connect." When a user touches the "connect" button 250, then the portable display device 200 may initiate an algorithm to search for wireless signals generated by medical devices, such as inflation devices. By contrast, when the portable display device 200 is connected to an inflation device and is receiving and processing the wireless transmission data, then the connect/disconnect button 250 may display "disconnect." When a user touches the "disconnect" button 250, then the portable display device 200 may stop processing wireless signals from the inflation device.

In some instances the portable display device 200 may be configured to automatically connect to an inflation device when the inflation device begins transmitting data. Alternatively, the inflation device may be configured with a bar code or a QR code configured to provide connection data to the portable display device 200. For example, the inflation device 100 of FIG. 4 may have a bar code, a QR code, or some other computer-readable information attached directly to the inflation device 100 and/or attached to packaging of the inflation device 100. The portable display device 200 may be configured with one or more components configured to read this information. For example, the portable display device 200 may comprise a camera. A user could position the camera such that it reads the bar code or QR code. The bar code or QR code could directly provide information regarding connection of the inflation device 100 to the portable display device 200. Additionally, or alternatively, a bar code or QR code may indirectly provide information by directing the device to an internet or a network location to obtain data, and/or may provide information (e.g., operating parameters of the inflation device or a coupled medical device) other than connection information.

In some instances, an inflation device 100 may not be configured with a bar code or a QR code, and/or the user may not be successful in connecting the inflation device 100 and portable display device 200 using that information. Thus, in some instances, a user may manually begin a connection sequence. In some instances, for example, the portable display device 200 may be coupled to computer-readable memory that has information (e.g., connection information, operating parameters, etc.) related to the inflation device 100 or an attached medical device (e.g., a balloon). A user may select the inflation device or medical device from a menu on the portable display device 200 to access the information and connect the devices.

In some instances, the inflation device 100 may be configured with an indicator configured to communicate the connection status of the inflation device 100. For example, in FIG. 4, an indicator light 153 is coupled to the sensor component 150. This indicator light 153 may comprise a light emitting diode (LED) or other light, or may comprise a mechanical indicia, such as an arrow or other member disposed in a particular orientation when the inflation device 100 is connected. In some instances multiple LED lights may be used. For example, the indicator may emit red light when the device is powered but not connected and green light when the inflation device 100 is connected with (for example, wirelessly paired with) the portable display device 200.

In other embodiments, an indicator including an LED indicator, such as indicator light 153, may be coupled to the sensor component 150 and oriented such that light from the indicator light 153 is directed into the fluid 50 disposed within the inflation device 100. The indicator light 153 may be positioned on an inside surface of the sensor component 150, for example, and/or the body of the inflation device 100 may be configured to transmit light to the fluid 50. In such embodiments the fluid 50, inflation device 100, and indicator light 153 may each be configured such that fluid 50 within the inflation device 100 tends to reflect light within the fluid 50, tending to cause the fluid 50 to appear illuminated when the indicator light 153 is on. In this manner the indicator light 153 can create a more visible indication of the status of the inflation device 150 while simultaneously indicating the amount of fluid 50 within the inflation device 100 by illuminating the fluid.

The portable display device 200 may be configured to display pressure data associated with prior inflations of the inflation device for a particular patient.

The portable display device 200 may be configured to transmit pressure data to a computer that stores patient data. The transmission may be via any number of known transmission means. For example, the transmission may be via email or a file transfer protocol or may be via a standardized medical records protocol. An example of a standardized medical protocol is HL7 v3.0. For the sake of clarity, it should be understood the portable display device 200 may receive a wireless signal, such as a Bluetooth signal, from the transmitter of an inflation device, convert that signal into pressure data, and then transmit the pressure data via a wireless signal, such as a Wi-Fi signal, to a server (such as a cloud server) that stores patient data.

In addition to transmission of data through Wi-Fi, Bluetooth, or other signals discussed above, the inflation device 100 may be configured to transmit data via pulsed infrared or visible light. For example, in some embodiments, an LED configured to transmit data may be coupled to the sensor component 150. This transmission LED may be disposed at the same location as the indicator light 153 and, in some embodiments, may comprise the indicator light 153. In other embodiments, these features may be separate. The transmission LED may be configured to emit pulses of light configured to carry data. These pulses may be sufficiently rapid that the LED appears to be continuously on to the naked eye. The length of the pulses, or length of spaces between the pulses, could be configured to relay data (for example as "1s" and "0s") to a remote sensor. The remote sensor may then convert this data to provide visual, audible, or other output.

The portable display device 200 may be configured to integrate pressure data from the inflation device into a patient's medical records. The portable display device 200 may also be configured to connect with a printer and print pressure data transmitted by the inflation device.

The portable display device 200 may be configured to toggle the display of the pressure data between different pressure units.

The portable display device 200 may be configured to receive input of patient information associated with the pressure data.

The portable display device 200 may be configured to receive input of a medical device type to be inflated by the inflation device, such as a medical balloon. In some embodiments, the portable display device 200 is configured to allow selection of a type of medical balloon to be inflated by the inflation device. The portable display device 200 may be connected to computer-readable memory storing information regarding various inflation devices, such as balloons. A user may select a particular device from a menu on the portable display device 200 and/or read a bar code or QR code using a camera or other reader on the portable display device 200, and the device could then access the appropriate stored data. This data may be stored remotely and accessed via a network.

In some embodiments, selection of a specific balloon alters the graphic displayed by the portable display device 200. For example, in FIGS. 5A-5C, the markers 230 denote approximately 45 psi increments of pressure. However, if a medical balloon is selected on the portable display device 200 that has a maximum pressure of 100 psi, then each of the markers 230 may be configured to represent 20 psi increments of pressure. The arrow 220 would then move further around the regions 242, 244, and 246 at much lower pressures than illustrated in FIGS. 5A-5C.

The portable display device 200 may be configured to allow illumination of the display of the pressure data in low-light or no-light settings. The illumination may be adjusted by a user, or, in some embodiments, the portable display device 200 may utilize a camera to detect light levels in the room and adjust illumination accordingly.

The portable display device 200 may be configured to provide audible signals when a desired maximum inflation is reached and/or audible signals as predetermined pressure levels are reached. The portable display device 200 and/or a connected processor may be configured to record and/or display the inflation history during a procedure. In some instances, a medical device may be configured to follow a particular inflation sequence over time. The portable display device 200 could display the desired sequence and track the actual progress along the sequence in real time. Additionally, the portable display device 200 could be configured to audibly call out inflation data, using voice or speech synthesis. This could cut down on errors or mistakes that may be made when an operator vocally calls out data to another individual who records the data. In some instances the data call out could be automatic, for example, the portable display device 200 may be configured to call out inflation data following a particular input, for example, several seconds after a user pulls negative pressure to deflate a balloon, the device could call out the peak inflation pressure preceding the deflation.

The portable display device 200 may be configured to respond to voice commands from a user of the inflation device to perform a function of the portable display device 200. For example, a user may use voice commands to have the portable display device 200 initiate a search for inflation devices transmitting wireless signals in the vicinity of the portable display device 200 or change illumination. Any of the functions of the portable display device 200 discussed herein may be activated or deactivated by voice commands.

Figure 6:
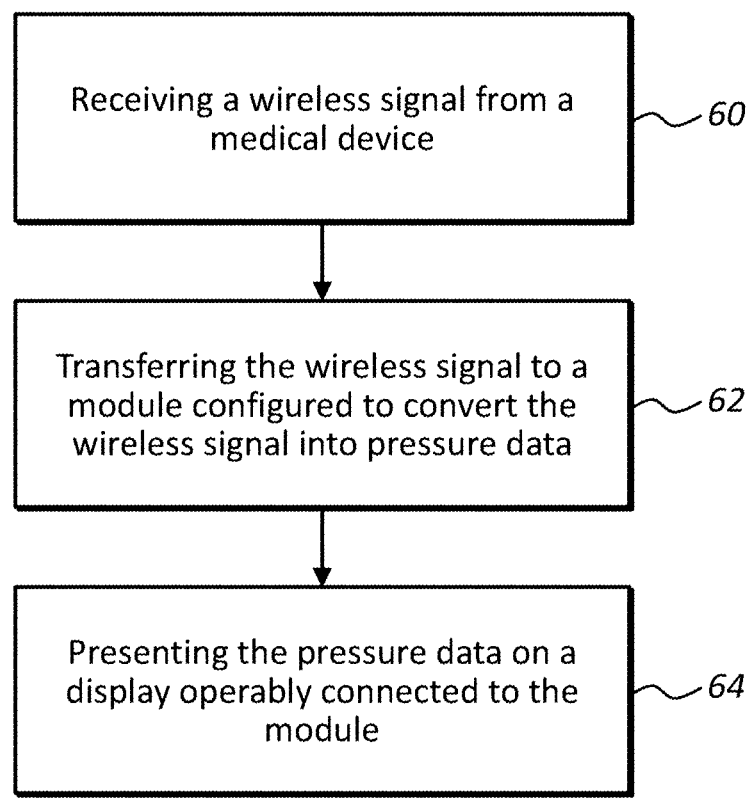
FIG. 6 illustrates a flow chart of one embodiment of a method of remotely displaying pressure data from a medical device.

FIG. 6 illustrates a method of remotely displaying pressure data from a medical device. In the illustrated embodiment, the method begins at the step 60 with receiving a wireless signal from a medical device. Next, the step 62 comprises transferring the wireless signal to a converter module configured to convert the wireless signal into pressure data. Thereafter, the step 64 comprises presenting the pressure data on a display operably connected to the converter module.

The method may further comprise additional steps before, after, and/or in between the steps 60, 62, and 64. For example, the method may further comprise presenting a numeric indication of pressure data, such as the current inflation pressure within the medical device. The method may also further comprise presenting a non-numeric indication of pressure data. The non-numeric indication of pressure data may indicate whether the current pressure is likely safe, potentially unsafe, or likely unsafe for the medical device.

In some embodiments, the medical device comprises an inflation device.

In some embodiments, the converter module is configured to determine a user's selected pressure units.

Additional steps may also comprise storing in a memory device pressure data associated with prior inflations of the medical device for a particular patient.

Additional steps may also comprise transmitting pressure data via a wireless transmitter to a computing device that stores patient data. Any number of transmission protocols may be used; for example, the transmission may be via an email protocol or via a standardized medical records protocol.

Additional steps may also comprise activating a records module to integrate the pressure data into a patient's medical records.

Additional steps may also comprise activating a rendering module to generate a printable image of the pressure data and sending a wireless signal to a printer or a print server of the printable image.

Additional steps may also comprise receiving input from a user on desired pressure units to be presented on the display. Other optional inputs include receiving user input of patient information associated with the wireless signal received from the medical device and receiving input from a user of the type of medical device to be inflated by the inflation device.

Additional steps may also comprise illuminating the display of the pressure data in low-light or no-light settings.

Additional steps may also comprise activating an alert system configured to generate an audible signal when a desired maximum inflation is reached and/or when predetermined pressure levels are reached.

Additional steps may also comprise powering a voice recognition system configured to detect a voice command from a user of the medical device, wherein the voice recognition system is configured to determine a module to be activated to accomplish the voice command.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless otherwise specified.

Embodiments may include various features, which may be embodied in machine-executable instructions executed by a general-purpose or special-purpose computer (or other electronic device). Alternatively, the features may be performed by hardware components that include specific logic for performing the steps or by a combination of hardware, software, and/or firmware.

Accordingly, the various components, modules, systems, and/or features described herein may be embodied as modules within a system. Such a system may be implemented in software, firmware, hardware, and/or physical infrastructure. Although not always explicitly named herein, a module may be identified (named) based on a function it performs. For example, a module that is configured to display something may comprise specific hardware, software, or firmware and be properly referred to as a "display module."

Embodiments may also be provided as a computer program product including a non-transitory machine-readable medium having stored thereon instructions that may be used to program, or be executed on, a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable media suitable for storing electronic instructions. Moreover, a computer program product may be run, executed, downloaded, and/or otherwise used locally or remotely via a network.

Figure 7:
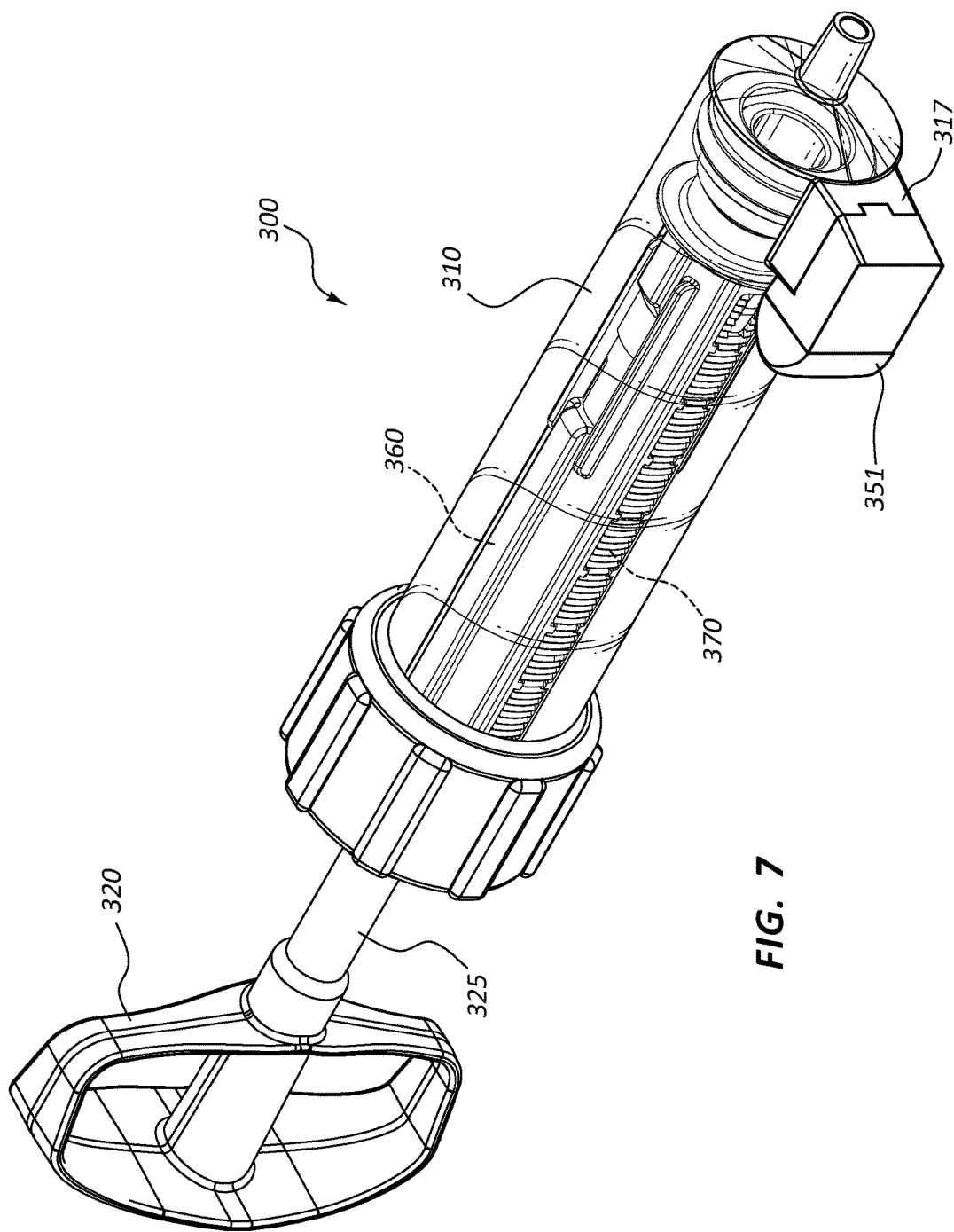
FIG. 7 is a perspective view of an inflation device with a pressure sensor and a wireless transmitter.
Figure 8:
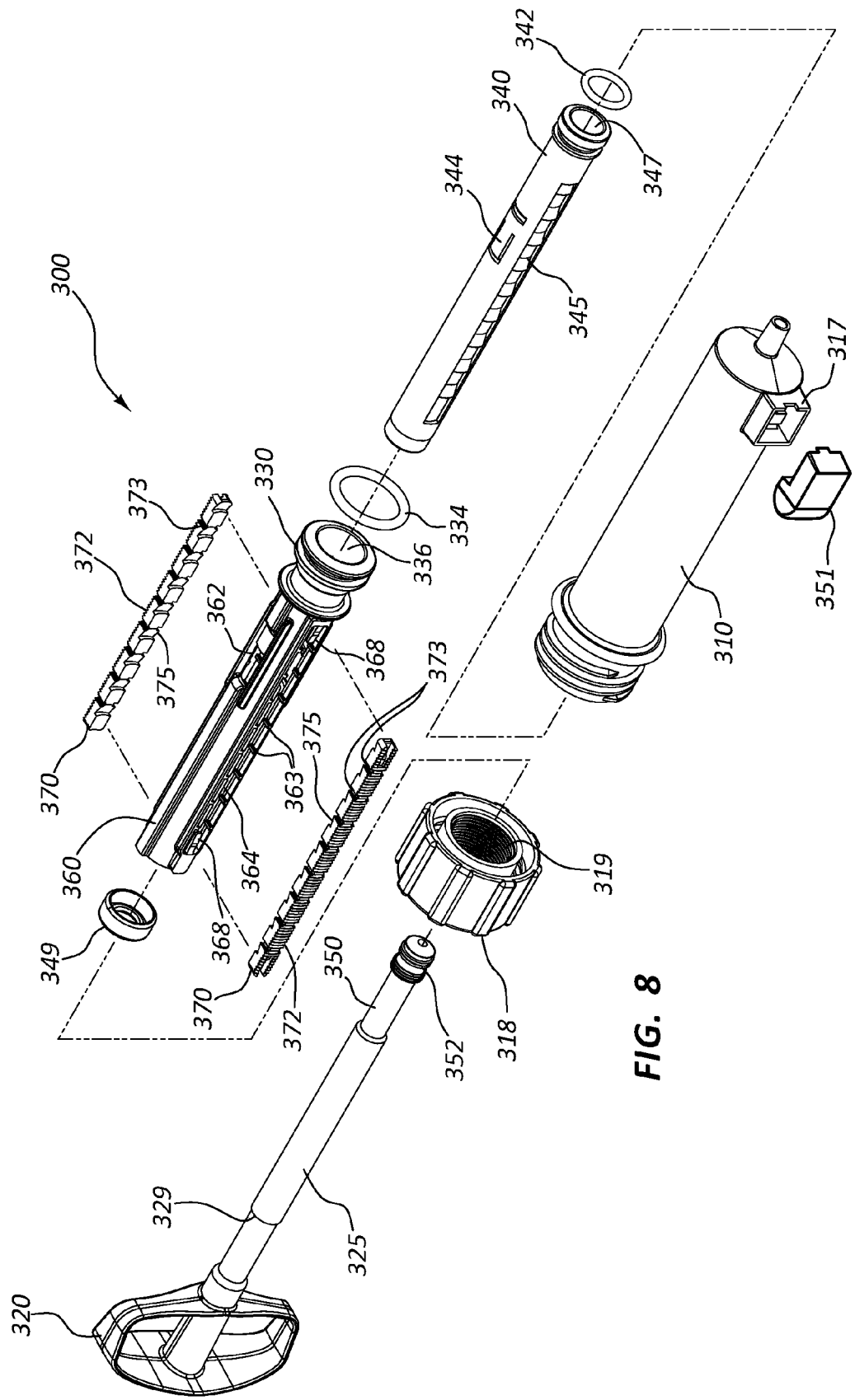
FIG. 8 is an exploded view of the inflation device of FIG. 7.

It should be understood that the pressure sensor 156 and wireless transmitter 158 disclosed above may be used with a variety of inflation devices. For example, FIGS. 7 and 8 illustrate an inflation device 300. The inflation device 300 of FIG. 7 may comprise a body portion, a syringe body 310, and a handle 320. A shaft 325 extends from the handle 320. Locking rails 370 and a locking sleeve 360 are also shown in FIG. 7. The embodiment of FIG. 7 comprises a sensor mounting bracket 317 on the syringe body 310. The sensor mounting bracket 317 may be configured to mate with a housing 351. The housing 351 may be the same as or similar to the housing 151 discussed above in relation to the inflation device 100. The housing 351 may be configured to receive a sensor assembly that is the same or similar to the sensor assembly 154 discussed above in relation to the inflation device 100. All of the disclosure above regarding the housing 151 and the sensor assembly 154 is applicable to the inflation device 300.

FIG. 8 is an exploded view of the inflation device 300 of FIG. 7. The exploded view of FIG. 8 illustrates the various components of the inflation device 300. The inflation device 300 of FIG. 8 comprises the syringe body 310 and a cap 318 that may be configured with locking threads 319.

The inflation device 300 further comprises a handle 320 and shaft 325 that are integrally formed with an inner plunger 350 that is coupled to an inner plunger seal 352. Similarly, in the embodiment of FIG. 8, a locking sleeve 360 is integrally formed with an outer plunger 330.

An outer plunger seal 334 may be provided in connection with the outer plunger 330 that may further define an interior portion 336 of the outer plunger 330. An intermediate plunger 340 and an intermediate plunger seal 342 may be configured to be disposed within the interior portion 336 of the outer plunger 330. The intermediate plunger 340 may also define an interior portion 347, with the inner plunger 350 configured to be disposed therein.

The intermediate plunger 340 may comprise intermediate plunger angled surfaces 345 configured to function in connection with locking rail angled surfaces 375 provided on the locking rails 370. Further, the inflation device 300 may be configured with engagement arms 344 disposed on the intermediate plunger 340 configured to function in connection with windows 362 in the locking sleeve 360.

The locking rails 370 may comprise locking rail threads 372 configured to engage the locking threads 319 of the cap 318. The locking sleeve 360 may comprise slots 364 configured to receive the locking rails 370. Mating grooves 373 and ridges 363 on these components may be disposed such that movement of the locking rails 370 with respect to the locking sleeve 360 is constrained. Further, biasing elements 368 may be coupled to the locking sleeve 360 and configured to interact with the locking rails 370.

Finally, the inflation device 300 may comprise an intermediate plunger cap 349 configured to be coupled to the proximal end of the intermediate plunger 340 when the inflation device 300 is assembled. The intermediate plunger cap 349 may be configured to contact a shaft shoulder 329 on the shaft 325 when the handle 320 is retracted proximally. Contact between the shaft shoulder 329 and the intermediate plunger cap 349 may be configured to likewise draw back the intermediate plunger 340 when the shaft shoulder 329 and the intermediate plunger cap 349 are in contact with each other.

Further, the locking sleeve 360 and intermediate plunger 340 are releasably coupled to each other in the unlocked configuration by a detent. Operation of the detent is further discussed in U.S. Provisional Patent Application No. 61/704,299, filed Sep. 21, 2012, and in U.S. patent application Ser. No. 14/021,054, filed Sep. 9, 2013 and titled "Variable Displacement Inflation Devices and Methods of Use," and the contents of both applications are incorporated herein by reference in their entirety.

Figure 9:
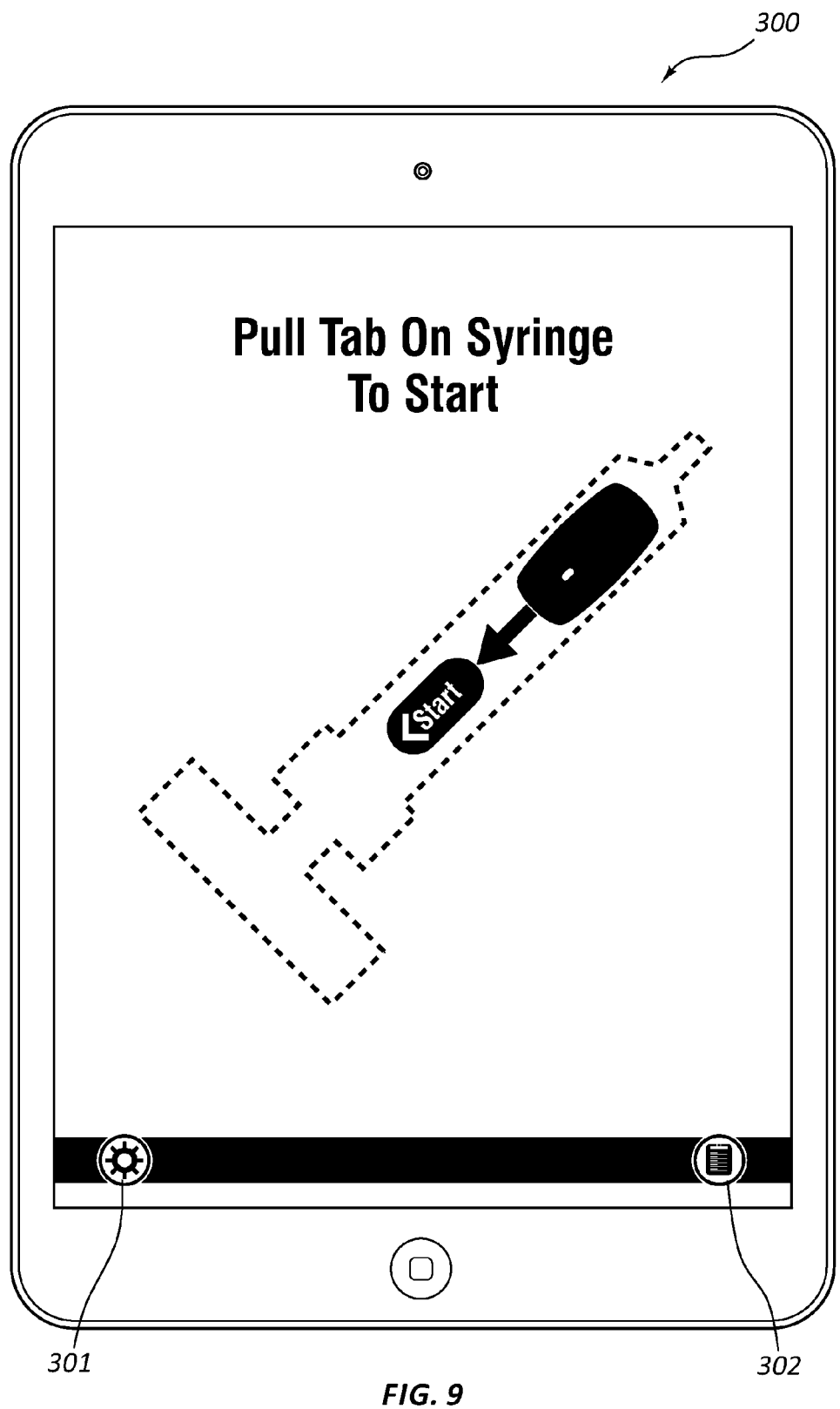
FIG. 9 is a front view of another embodiment of a remote display device in a first configuration.
Figure 10:
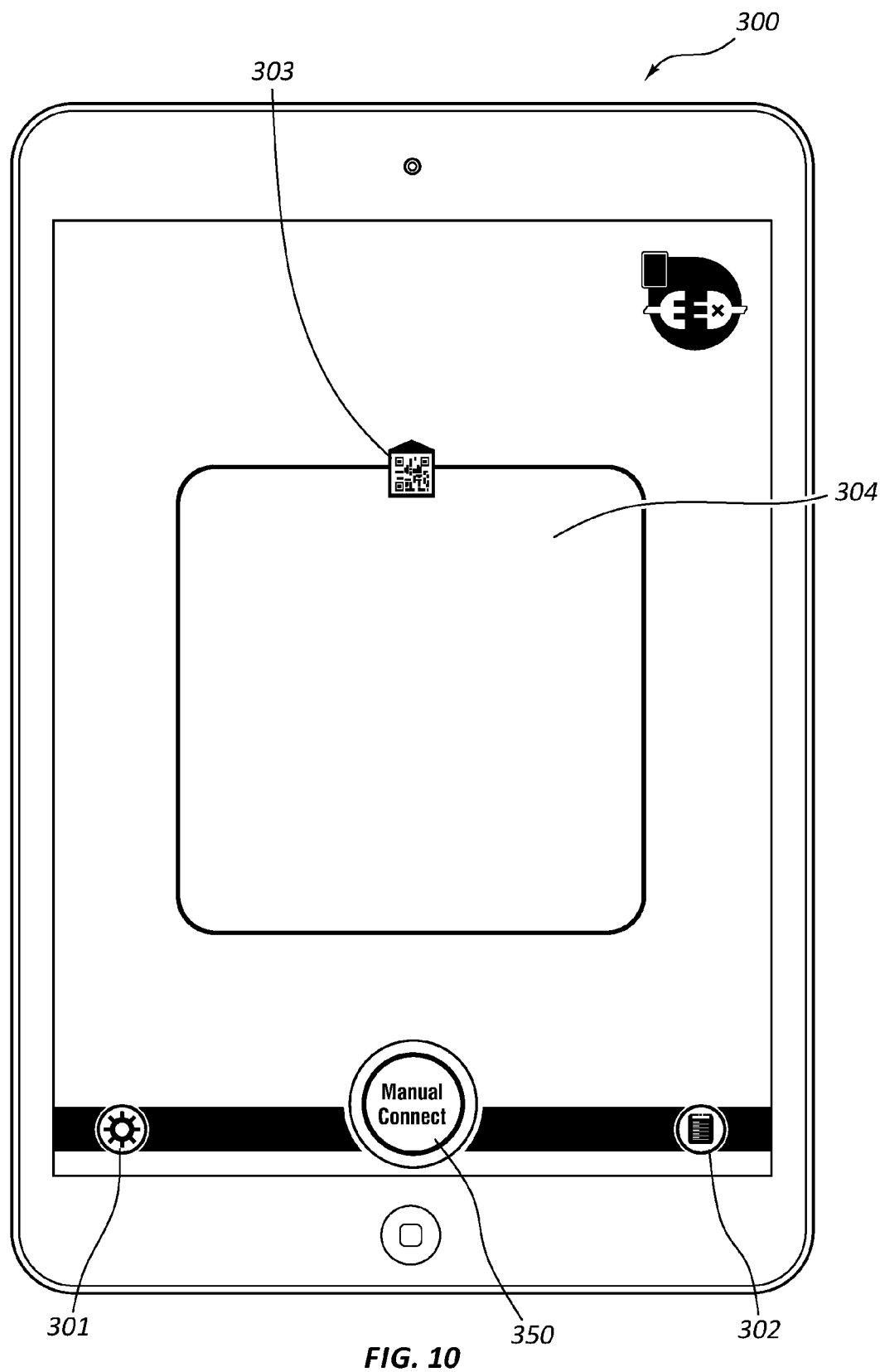
FIG. 10 is a front view of the remote display device of FIG. 9 in a second configuration.
Figure 11:
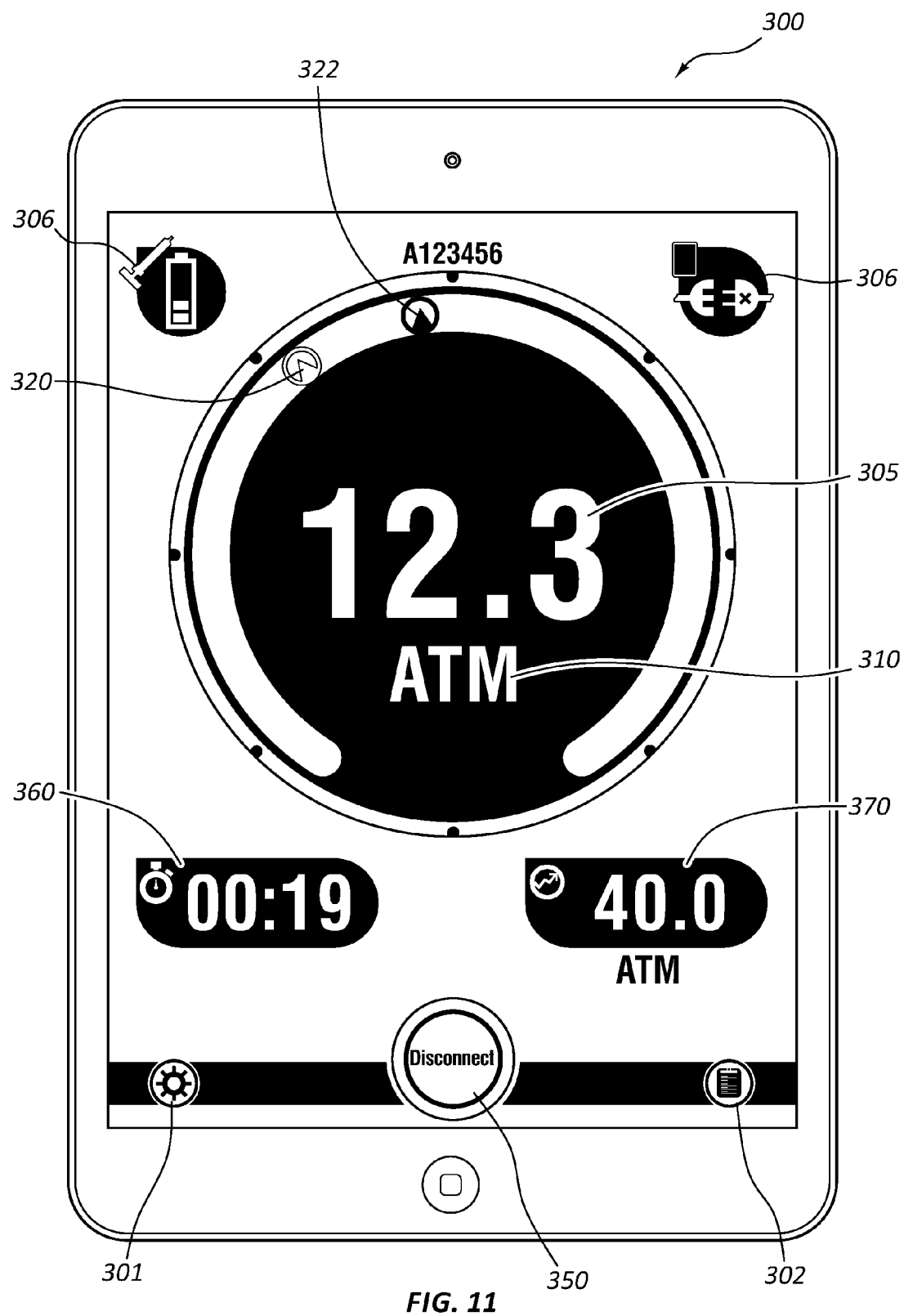
FIG. 11 is a front view of the remote display device of FIG. 9 in a third configuration.

Remote display devices may further be configured to display instructors and/or guide a user during set up or use of any of the devices or systems disclosed herein. FIGS. 9-11 illustrate exemplary displays that may be so configured. Any other set of instructions, inflation data, or information may be displayed during use of the systems and devices disclosed herein. FIG. 9 is a front view of another embodiment of a remote display device 300 in a first configuration, FIG. 10 is a front view of the remote display device 300 in a second configuration, and FIG. 11 is a front view of the remote display device 300 in a third configuration.

As shown in FIG. 9, the remote display device 300, which may comprise a portable display device, can be configured such that it initially displays information relative to the set up of an inflation device or system. For example, the remote display device 300 may indicate to a user how to power up a sensor component on an inflation device and/or how to begin wirelessly connecting the inflation device to the remote display device 300. Additionally, the remote display device 300 may include a settings icon 301 or a history icon 302 to display settings or inflation history of the system. Other features or icons could also be included.

In the state of FIG. 9, the remote display device 300 may be searching for devices to connect to, or may be configured to wait for user input to do so. In some instances, the remote display device 300 will automatically respond when an inflation device is activated or powered up within range of the remote display device 300 and prompt a user regarding connection to that device.

As shown in FIG. 10, the remote display device 300 may be configured to aid in connecting the remote display device 300 to an inflation device or other medical device. For example, the remote display device 300 may automatically activate a camera on the remote display device 300 when an active inflation device is within range. In the illustrated embodiment, a QR code icon 303 is shown in this state to communicate to a user to position the camera such that an image of a QR code on the desired inflation device is relayed from the camera and shown in a viewing portion 304 of the remote display device 300. In some instances, multiple inflation devices may be within range (e.g., previously used devices or devices in adjacent rooms). The remote display device 300 may be configured such that, when the QR code is displayed in the viewing portion 304, the remote display device 300 automatically connects to the associated device. The same technique may be used with bar codes or other computer-readable displays on the inflation device.

The remote display device 300 may further comprise a connect/disconnect button 350. When the remote display device 300 is in the configuration of FIG. 10, the connect/disconnect button 350 may be configured to override the camera/automatic connection and allow a user to manually connect an active device in range. For example, if no device is connected, activation of the connect/disconnect button may bring up a list or menu of all available devices within range. A user could then manually select the desired device.

Once a device is connected, the connect/disconnect button may change (e.g., change to "disconnect") to indicate the devices are connected (for example by Bluetooth pairing). An indicator on the inflation device (e.g., an LED) may also be configured to communicate that the devices are connected.

In the configuration of FIG. 11, the remote display device 300 is wirelessly connected to an inflation device and information regarding the inflation device is shown in the remote display device 300. For example, the connect/disconnect button 350 indicates a device is connected. The remote display device 300 may display numeric pressure data 305, display units 310, and non-numeric pressure data, such as by arrow 320. Another arrow 322 may be configured to indicate, non-numerically, peak pressure, desired pressure, or any other predetermined pressure. Additionally, a portion of the remote display device 300 may indicate peak pressure 370 numerically, as well as display a clock 360 that tracks the inflation sequence or medical procedure. Additional portions of the remote display device 300 may indicate various information such as battery life, power connection status, and so forth. Information icons 306 represent these displays, and icons representing various data are within the scope of this disclosure.

During or after a procedure, it is within the scope of this disclosure for the remote display device 300 to further transmit inflation data to an auxiliary device. For example, the remote display device 300 can send inflation data to a hospital computer, patient records, or other locations. The remote display device 300 can be configured to interact with standard hospital data storage components or computers. In some embodiments, the remote display device 300 can be configured to output data directly to existing or standard auxiliary devices, for example, by emulating an input device (e.g., a keyboard) for the existing device.

Exemplary Embodiments

The following embodiments are illustrative and exemplary and not meant as a limitation of the scope of the present disclosure in any way.

I. Inflation Devices

In one embodiment an inflation device configured for use with a medical device comprises: (1) a body component; (2) a pressurization component configured to increase or decrease pressure within the body component by displacing the pressurization component with respect to the body component; (3) an actuator operably connected to the pressurization component and configured to displace the body component; (4) a pressure sensor in communication with the body component and configured to measure pressure within the body component; and (5) a transmitter in communication with the pressure sensor and configured to transmit a wireless signal representative of the pressure measured by the pressure sensor.

The transmitter may be configured to transmit radio waves.

The transmitter may be configured as a Bluetooth transmitter.

The transmitter may be configured as a Wi-Fi transmitter.

The transmitter may be configured to transmit visible light.

The transmitter may be configured to transmit infrared waves.

The transmitter may be configured as a sound wave transmitter.

The inflation device may further comprise a sensor assembly that comprises the pressure sensor and the transmitter.

The sensor assembly may further comprise a battery.

The sensor assembly may further comprise a pull tab configured to electrically isolate the battery from a circuit board when the pull tab is in place.

The pull tab may be configured to be removable, and the sensor assembly may be configured to continuously transmit pressure data when the pull tab is removed.

The sensor assembly may further comprise an on/off switch configured to control conduction of electrical energy from the battery, wherein when the switch is in the "on" position, the sensor assembly is configured to continuously transmit pressure data.

The switch may comprise a momentary switch.

The switch may comprise a momentary trigger or momentary button.

The momentary switch may be configured to transition the inflation device out of a sleep or power save mode.

The pressure sensor may be in direct communication with an interior portion of the body component.

The pressure sensor may be isolated from communication with the environment external to the body component.

The inflation device may further comprise a seal configured to isolate the pressure sensor from the environment external to the body component.

An aperture may extend through a sidewall of the body component, the aperture configured to provide communication with the pressure sensor.

The seal may be disposed around the aperture.

The inflation device may further comprise a housing coupled to the body component, the housing configured to receive the sensor assembly.

Friction between the housing and the sensor assembly may couple the sensor assembly to the housing.

The sensor assembly may be coupled to the housing in a snap fit configuration.

The snap fit may provide pressure on the seal member.

The sensor assembly may comprise a circuit board, and the pressure sensor may be directly coupled to the circuit board.

The pressure sensor may be coupled to a first side of the circuit board, and a circuit board aperture may provide communication between a second side of the circuit board and the pressure sensor.

The transmitter may be coupled directly to the circuit board.

The transmitter may be coupled directly to the first side of the circuit board.

The transmitter may be coupled to a first side of the circuit board, and the pressure sensor may be coupled to a second side of the circuit board, wherein the pressure sensor is in direct communication with an interior portion of the body component.

The inflation device may be configured for inflation of a medical device.

The inflation device may further comprise a coupling member configured to selectively constrain the displacement of the pressurization component with respect to the body component.

The actuator may be further configured to selectively engage and disengage the coupling member.

The actuator may be configured to provide a mechanical advantage in engaging or disengaging the coupling mechanism.

The actuator may be configured to disengage the coupling mechanism in response to a proximally oriented force on the actuator.

The body component may comprise a syringe body.

The pressurization component may comprise a plunger configured to form a slidable seal with an internal surface of the syringe body and configured for insertion and retraction within the syringe body.

The coupling member may comprise coupling member threads configured to constrain movement of the plunger within the syringe body and wherein the plunger is configured to selectively engage and disengage with the coupling member threads.

A shaft of the plunger may comprise plunger threads configured to be selectively engaged with the coupling member threads.

The plunger shaft may be configured to screw into or out of the syringe body when the plunger threads are engaged with the coupling member threads.

The plunger shaft may be configured to slide into or out of the syringe body when the plunger threads are disengaged from the coupling member threads.

The plunger threads may be formed on a thread rail configured for retraction from or advancement to the surface of the plunger shaft.

The actuator may be operably coupled to the thread rail and configured to selectively retract and advance the thread rail.

The inflation device may further comprise a handle operably coupled to the plunger shaft and to the actuator.

The handle may be configured to provide a mechanical advantage when retracting the thread rail with the actuator.

The handle may further comprise a lever operably connected to the actuator, wherein the lever is configured to provide a mechanical advantage when retracting the thread rail with the actuator.

The inflation device may further comprise a second plunger disposed within the plunger.

The plunger may comprise an outer plunger and an intermediate plunger, and the outer plunger and the intermediate plunger may be releasably coupled to each other.

The inflation device may further comprise a locking sleeve disposed around the intermediate plunger, wherein the locking sleeve is coupled to the outer plunger and the locking sleeve is releasably coupled to the intermediate plunger.

Displacement of the locking sleeve with respect to the intermediate plunger may be configured to selectively couple the locking sleeve and the intermediate plunger to the syringe body.

The locking sleeve may be configured to automatically decouple from the intermediate plunger when pressure within the syringe body is at or above a first pressure.

The inflation device may further comprise a detent operably coupling the locking sleeve to the intermediate plunger.

The magnitude of the first pressure at which the locking sleeve automatically decouples from the intermediate plunger may be adjustable by a user.

The locking sleeve may be configured to manually decouple from the intermediate plunger when pressure within the reservoir is at or above a first pressure.

The second plunger may be releasably coupled to the plunger.

Displacement of the locking sleeve with respect to the intermediate plunger may be configured to decouple the second plunger from the first plunger.

Displacement of the locking sleeve with respect to the intermediate plunger may be configured to releasably couple the plunger to the syringe body.

The inflation device may further comprise one or more thread rails, and the thread rails may be configured to releasably couple the first plunger to the syringe body.

The pressure sensor may comprise a pressure transducer.

II. Inflation Kits

In one embodiment an inflation kit may comprise: (1) an inflation device configured for use with a medical device, and the inflation device may comprise: (a) a body component comprising a cavity; (b) a pressurization component configured to increase or decrease pressure within the cavity of the body component by displacing the pressurization component with respect to the body component; (c) a pressure sensor in communication with the body component and configured to measure pressure within the cavity of the body component; and (d) a transmitter in communication with the pressure sensor and configured to transmit a wireless signal representative of the pressure measured by the pressure sensor; and (2) a remote display device configured to receive the wireless signal transmitted by the inflation device transmitter and also configured to display real-time pressure data within the body component.

The remote display device may comprise a portable display device.

The remote display device may be configured to display a numeric indication of pressure data.

The numeric indication may comprise a current inflation pressure within the cavity of the body component.

The remote display device may also be configured to display a non-numeric indication of pressure data.

The non-numeric indication of pressure data may indicate whether the current pressure is likely safe for the medical device attached to the inflation device.

The non-numeric indication of pressure data may indicate whether the current pressure is potentially unsafe for the medical device attached to the inflation device.

The non-numeric indication of pressure data may indicate whether the current pressure is likely unsafe for the medical device attached to the inflation device.

The remote display device may comprise a desktop computer.

The remote display device may comprise a hand-held computer.

The hand-held computer may comprise a tablet computer.

The remote display device may comprise a touchscreen graphic user interface.

The remote display device may be configured to display pressure data associated with prior inflations of the inflation device for a particular patient.

The remote display device may be configured to transmit pressure data to a computer that stores patient data.

The transmission may be via email.

The transmission may be via a standardized medical records protocol.

The remote display device may be configured to integrate pressure data from the inflation device into a patient's medical records.

The remote display device may be configured to connect with a printer and print pressure data transmitted by the inflation device.

The remote display device may be configured to toggle the display of the pressure data between different pressure units.

The remote display device may be configured to receive input of patient information associated with the pressure data.

The remote display device may be configured to receive input of a medical device type to be inflated by the inflation device.

The remote display device may be configured to receive input of a type of medical balloon.

The remote display device may be configured to allow selection of a type of medical balloon to be inflated by the inflation device.

The remote display device may be configured to allow illumination of the display of the pressure data in low-light or no-light settings.

The remote display device may be configured to provide audible signals when a desired maximum inflation is reached.

The remote display device may be configured to provide audible signals as predetermined pressure levels are reached.

The remote display device may be configured to respond to voice commands from a user of the inflation device to perform a function of the portable display device.

III. Methods

In one embodiment, a method of remotely displaying pressure data from a medical device may comprise: (1) receiving a wireless signal from a medical device; (2) transferring the wireless signal to a converter module configured to convert the wireless signal into pressure data; and (3) presenting the pressure data on a display operably connected to the converter module.

The method may further comprise presenting a numeric indication of pressure data.

The numeric indication may comprise a current inflation pressure within the medical device.

The method may further comprise presenting a non-numeric indication of pressure data.

The non-numeric indication of pressure data may indicate whether the current pressure is likely safe for the medical device.

The non-numeric indication of pressure data may indicate whether the current pressure is potentially unsafe for the medical device.

The non-numeric indication of pressure data may indicate whether the current pressure is likely unsafe for the medical device.

The medical device may comprise an inflation device.

The converter module may be configured to determine a user's selected pressure units.

The method may further comprise storing in a memory device pressure data associated with prior inflations of the medical device for a particular patient.

The method may further comprise transmitting pressure data via a wireless transmitter to a computing device that stores patient data.

The transmission may be via an email protocol.

The transmission may be via a standardized medical records protocol.

The method may further comprise activating a records module to integrate the pressure data into a patient's medical records.

The method may further comprise activating a rendering module to generate a printable image of the pressure data and sending a wireless signal to a printer or a print server of the printable image.

The method may further comprise receiving input from a user on desired pressure units to be presented on the display.

The method may further comprise receiving input from a user of patient information associated with the wireless signal received from the medical device.

The method may further comprise receiving input from a user of the type of medical device.

The method may further comprise illuminating the display of the pressure data in low-light or no-light settings.

The method may further comprise activating an alert system configured to generate an audible signal when a desired maximum inflation is reached.

The method may further comprise activating an alert system configured to generate an audible signal when predetermined pressure levels are reached.

The method may further comprise powering a voice recognition system configured to detect a voice command from a user of the medical device, wherein the voice recognition system is configured to determine a module to be activated to accomplish the voice command.

IV. Display Apparatus

In one embodiment, an apparatus to display pressure data received from a medical device may comprise: (1) a signal module to receive a wireless signal from the medical device, the wireless signal including data from a pressure measurement obtained by the medical device; (2) a converter module to convert the wireless signal to extract the data and generate pressure data; and (3) a display operably coupled to the converter module and configured to present a graphical display of the pressure data, the graphical display including a numeric display that provides a numeric indication of a current inflation pressurization within the medical device and a plurality of non-numeric indicia which are actuated to provide a non-numeric representation of the current inflation pressurization.

The non-numeric indicia may simultaneously indicate whether the current inflation pressurization is likely safe, potentially unsafe, or likely unsafe.

Without further elaboration, it is believed that one skilled in the art can use the preceding description to utilize the present disclosure to its fullest extent. The examples and embodiments disclosed herein are to be construed as merely illustrative and exemplary, and not as a limitation of the scope of the present disclosure in any way. It will be apparent to those having skill in the art that changes may be made to the details of the above-described embodiments without departing from the underlying principles of the disclosure herein. It is intended that the scope of the invention be informed by the claims appended hereto and their equivalents.

The invention claimed is:

1. An inflation kit comprising:
an inflation device configured for use with a medical device, the inflation device comprising:
a body component comprising a cavity;
a pressurization component configured to increase or decrease pressure within the cavity of the body component by displacing the pressurization component with respect to the body component;
a sensor component comprising:
a pressure sensor in communication with the body component and configured to measure pressure within the cavity of the body component;
a transmitter in communication with the pressure sensor and configured to transmit a wireless signal representative of the pressure measured by the pressure sensor; and
an indicator configured to communicate whether the inflation device is wirelessly connected to a portable handheld display device; and
the portable handheld display device configured to receive the wireless signal transmitted by the inflation device transmitter and also configured to display real-time pressure data within the body component, wherein the portable handheld display device is configured to display numeric and non-numeric indicia of pressure data, and wherein the non-numeric indicia comprises color-coded indicia to indicate when the pressure has reached a predetermined pressure.

2. The inflation kit of claim 1, wherein the portable handheld display device is configured to indicate a relationship between current pressure and one or more parameters of the medical device coupled to the inflation device.

3. The inflation kit of claim 2, wherein parameters of one or more medical devices are stored in a computer coupled to the portable handheld display device.

4. The inflation kit of claim 1, wherein the portable handheld display device is configured to provide audible signals as predetermined pressure levels are reached.

5. The inflation kit of claim 1, wherein the portable handheld display device is configured to respond to voice commands from a user of the inflation device to initiate a search for inflation devices transmitting wireless signals in the vicinity of the portable handheld device.

6. The inflation kit of claim 1, wherein the indicator comprises an LED light configured to display two colors, corresponding to a first mode when the inflation device is turned on and not wirelessly connected to the portable handheld display device and a second color corresponding to a second mode when the inflation device is turned on and wirelessly connected to the portable handheld display device.

7. The inflation kit of claim 6, wherein the LED light is disposed on an inside surface of the sensor component and configured to direct light into the cavity.

8. The inflation kit of claim 7, wherein the LED light is configured to illuminate fluid disposed within the cavity.

9. The inflation kit of claim 1, wherein the portable handheld display device comprises a gauge configured to display pressure in increments.

10. The inflation kit of claim 1, wherein the portable handheld display device is a tablet.

11. The inflation kit of claim 1, further comprising computer readable information coupled to the inflation device, the computer readable information configured to provide connection data to the portable handheld display device.

12. The inflation kit of claim 11, wherein the computer readable information is a QR code.

13. The inflation kit of claim 1, wherein the non-numeric indicia comprises three distinct colored regions that correspond with distinct pressure ranges.

14. The inflation kit of claim 13, wherein the non-numeric indicia comprises a marker that is disposed within one of the three distinctly colored regions, and wherein the location of the marker indicates the pressure within the cavity of the body component.

15. The inflation kit of claim 1, wherein the predetermined pressure correlates with a parameter of the medical device.

* * * * *